(12) United States Patent
Basarab et al.

(10) Patent No.: US 6,504,058 B1
(45) Date of Patent: Jan. 7, 2003

(54) FUNGICIDAL AMIDES

(75) Inventors: Gregory S. Basarab, Sudbury, MA (US); Lee Dalton Jennings, Chestnut Ridge, NY (US); Dennis R. Rayner, Wilmington, DE (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 10/068,621

(22) Filed: Feb. 6, 2002

Related U.S. Application Data

(63) Continuation of application No. 09/581,702, filed as application No. PCT/US98/26014 on Dec. 8, 1998, now abandoned.
(60) Provisional application No. 60/069,458, filed on Dec. 15, 1997.

(51) Int. Cl.⁷ .................. C07C 233/58; A01N 37/18
(52) U.S. Cl. ............... 564/189; 514/365; 514/366; 514/372; 514/373; 514/408; 514/438; 514/624; 548/146; 548/152; 548/567; 549/76; 564/90; 558/414; 558/433
(58) Field of Search ................. 564/189, 190, 564/191; 514/624, 438, 365, 366, 372, 373, 408; 548/146, 152, 567; 558/414, 433; 549/76

(56) References Cited

U.S. PATENT DOCUMENTS 4,710,518 A * 12/1987 Kurahashi et al. .......... 514/626

FOREIGN PATENT DOCUMENTS

JP         62201855    * 9/1987

* cited by examiner

*Primary Examiner*—Shailendra Kumar
(74) *Attorney, Agent, or Firm*—Gilbreth & Associates, P.C.; J. M. (Mark) Gilbreth; Mary A. Gilbreth

(57) ABSTRACT

Compounds of Formula I are disclosed which are useful as fungicides

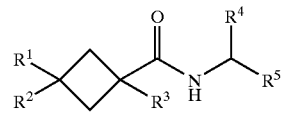

wherein
- $R^1$ is hydrogen; halogen; $C_1$–$C_2$ alkoxy; $C_1$–$C_2$ haloalkoxy; cyano; or $C_1$–$C_2$ alkyl optionally substituted with halogen, $C_1$–$C_2$ alkoxy or cyano;
- $R^2$ is hydrogen; halogen; or $C_1$–$C_4$ alkyl optionally substituted with halogen, $C_1$–$C_2$ alkoxy or cyano;
- $R^3$ is hydrogen; halogen; $C_1$–$C_4$ alkoxy; $C_1$–$C_4$ haloalkoxy; or $C_1$–$C_4$ alkyl optionally substituted with halogen, $C_1$–$C_2$ alkoxy or cyano; or
- $R^2$ and $R^3$ can be taken together as —$CH_2CH_2$—;
- $R^4$ is $C_1$–$C_2$ alkyl;
- $R^5$ is $R^6$, $CH(R^8)OR^6$, $CH(R^8)CH(R^7)R^6$ or $C(R^8)$=$C(R^7)R^6$; and
- $R^6$, $R^7$ and $R^8$ are as defined in the disclosure.

Also disclosed are compositions containing the compounds of Formula I and a method for controlling plant diseases caused by fungal plant pathogens which involves applying an effective amount of a compound of Formula I.

9 Claims, No Drawings

FUNGICIDAL AMIDES

REFERENCE TO RELATED APPLICATIONS

The present application is a Continuation of U.S. patent application Ser. No. 09/581,702 filed Feb. 20, 2001, entitled "Fungicidal Amides," now abandoned, which claims benefit of No. 60/069,458, filed Dec. 15, 1997, and is also a 371 of PCT/US98/26014, filed Dec. 8, 1998.

BACKGROUND OF THE INVENTION

This invention relates to certain fungicidal amides, their compositions, and methods of their use as fungicides.

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different modes of action.

Japanese Patent Application JP 2,233,654 and International Publication WO 97/35838 disclose certain amides and their use as fungicides. V. Prelog and J. Thix in *Helv. Chini. Acta* (1982), 65(8), 2622–44 disclose certain cyclobutane carboxamnides.

The fungicidal amides of the present invention are not disclosed in these publications.

SUMMARY OF THE INVENTION

This invention is directed to compounds of Formula I including all geometric and stereoisomers, agricultural compositions containing them and their use as fungicides:

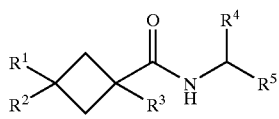

I wherein $R^1$ is hydrogen; halogen; $C_1$–$C_2$ alkoxy; $C_1$–$C_2$ haloalkoxy; cyano; or $C_1$–$C_2$ alkyl optionally substituted with halogen, $C_1$–$C_2$ alkoxy or cyano;

$R^2$ is hydrogen; halogen; or $C_1$–$C_4$ alkyl optionally substituted with halogen, $C_1$–$C_2$ alkoxy or cyano;

$R^3$ is hydrogen; halogen; $C_1$–$C_4$ alkoxy; $C_1$–$C_4$ haloalkoxy; or $C_1$–$C_4$ alkyl optionally substituted with halogen, $C_1$–$C_2$ alkoxy or cyano; or $R^2$ and $R^3$ can be taken together as —$CH_2CH_2$—;

$R^4$ is $C_1$–$C_2$ alkyl;

$R^5$ is $R^6$, $CH(R^8)OR^6$, $CH(R^8)CH(R^7)R^6$ or $C(R^8)=C(R^7)R^6$;

$R^6$ is phenyl; naphthalenyl; a 5- to 6-membered aromatic heterocyclic ring containing 1 to 2 heteroatoms selected from nitrogen, oxygen and sulfur; or a 9- to 10-membered fused aromatic bicyclic ring containing 1 to 2 heteroatoms each $R^6$ optionally substituted with one to three substituents selected from the group halogen, $C_1$–$C_4$ alkyl, $C_1$–$C_4$ haloalkyl, $C_1$–$C_4$ alkoxy, $C_1$–$C_4$ haloalkoxy, $Si(CH_3)_3$, cyano, NHC(=O)$R^9$ and NHC(=S)$R^9$;

$R^7$ is halogen, $C_1$–$C_4$ alkyl or $C_1$–$C_4$ haloalkyl;

$R^8$ is hydrogen; $C_1$–$C_6$ alkyl; phenyl optionally substituted with halogen, cyano, $C_1$–$C_3$ alkyl or $C_1$–$C_3$ alkoxy; or pyridinyl optionally substituted with halogen, cyano, $C_1$–$C_3$ alkyl or $C_1$–$C_3$ alkoxy; and each $R^9$ is hydrogen or $C_1$–$C_4$ alkyl;

provided that i) at least one of $R^1$, $R^2$ and $R^3$ is other than hydrogen; and ii) when $R^2$ and $R^3$ are taken together as —$CH_2CH_2$—, then $R^5$ is other than $R^6$.

DETAILS OF THE INVENTION

In the above recitations, the term "alkyl", used alone or in the compound words such as "haloalkyl" includes straight-chain or branched alkyl, such as, methyl, ethyl, n-propyl, i-propyl, or the different butyl, pentyl or hexyl isomers. "Alkoxy" includes, for example, methoxy, ethoxy, n-propyloxy, isopropyloxy and the different butoxy isomers.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The term "haloalkoxy" is defined analogously to the term "haloalkyl. Examples of "haloalkoxy" include $CF_3O$, $CCl_3CH_2O$, $HCF_2CH_2CH_2O$ and $CF_3CH_2O$.

The terms "aromatic" is defined as those rings or rings which satisfy the Hückel rule. The term "aromatic heterocyclic ring" includes aromatic heterocycles (where aromatic indicates that the Hückel rule is satisfied). The heterocyclic rings can be attached through any available carbon or nitrogen by replacement of a hydrogen on said carbon or nitrogen. Examples of 5- to 6-membered aromatic heterocyclic rings include thienyl, isothiazolyl, thiazolyl, pyrrolyl and pyridinyl. The term "fused aromatic bicyclic ring" includes fused aromatic heterocycles (where aromatic indicates that the Hückel rule is satisfied). Examples of fused aromatic bicyclic rings containing 1 to 2 heteroatoms include benzofuranyl, benzo[b]thiophenyl and benzothiazolyl.

The total number of carbon atoms in a substituent group is indicated by the "$C_i$–$C_j$" prefix where i and j are numbers from 1 to 4. For example, $C_1$–$C_2$ alkyl designates methyl and ethyl.

When a group contains a substituent which can be hydrogen, for example $R^1$ or $R^2$, then, when this substituent is taken as hydrogen, it is recognized that this is equivalent to said group being unsubstituted. When a group is optionally substituted with a substituent, (e.g., $C_1$–$C_2$ alkyl optionally substituted with halogen), then, when the group is not substituted with that substituent, it is recognized that this is equivalent to said group having a hydrogen substituent.

Compounds of this invention can exist as one or more stereoisomers. The various stereoisomers include enantiomers, diastereomers, and geometric isomers. One skilled in the art will appreciate that one stereoisomer may be more active and/or may exhibit beneficial effects when enriched relative to the other stereoisomer(s) or when separated from the other stereoisomer(s). Compounds of Formula I can exist as cis and trans cyclobutane isomers. This invention comprises cis/trans mixtures as well as the pure isomers. The compounds of this invention can exist as R and S enantiomers at the carbon to which $R^4$ and $R^5$ are attached. Of particular note are the compounds of Formula I having the R configuration. The R configuration is as defined by the Cahn-Ingold-Prelog system. (See March, J. *Advanced Organic Chemistry*; 3rd ed., John Wiley: New York, (1985).) This invention comprises racemic mixtures as well as pure enantiomers. Additionally, the skilled artisan knows how to separate, enrich, and/or to selectively prepare said stereoisomers. Accordingly, the present invention comprises all compounds selected from Formula I. The compounds of the invention may be present as a mixture of stereoisomers, individual stereoisomers, or as an optically active form.

Preferred compounds for reasons of better activity and/or ease of synthesis are:

Preferred 1
Compounds of Formula I above wherein
$R^1$ is halogen or $C_1$–$C_2$ alkyl optionally substituted with halogen;
$R^2$ is halogen or $C_1$–$C_2$ alkyl optionally substituted with halogen;
$R^3$ is halogen or $C_1$–$C_2$ alkyl optionally substituted with halogen;
$R^4$ is $CH_3$;
$R^5$ is $R^6$; and
$R^6$ is phenyl optionally substituted with one to two substituents selected from the group halogen, $C_1$–$C_4$ alkyl, $CF_3$, $C_1$–$C_4$ alkoxy, $C_1$–$C_4$ haloalkoxy and cyano.

Preferred 2
Most preferred compounds include compounds of Preferred 1 selected from the group

[1(R)-cis]-N-[1-(4-bromophenyl)ethyl]-3-chloro-3-methyl-1-(trifluoromethyl)cyclobutanecarboxamide;
[1(R)-trans]-N-[1-(4-bromophenyl)ethyl]-3-chloro-3-methyl-1-(trifluoromethyl)cyclobutanecarboxamide;
[1(R)-trans]-N-[1-(4-bromophenyl)ethyl]-3-chloro-3-methyl-1-(trifluoromethyl)cyclobutanecarboxamide;
[1(R)-trans]-3-chloro-N-[1-(4-chlorophenyl)ethyl]-3-methyl-1-(trifluoromethyl)cyclobutanecarboxamide;
[1(R)-trans]-3-chloro-N-[1-(2,4-dichlorophenyl)ethyl]-3-methyl-1-(trifluoromethyl)cyclobutanecarboxamide;
(1R)-N-[1-(4-bromophenyl)ethyl]-1,3,3-trichlorocyclobutanecarboxamide;
[1(R)-trans]-N-[1-(4-bromophenyl)ethyl]-3-chloro-1,3-dimethylcyclobutanecarboxamide;
[1(R)-cis]-N-[1-(4-bromophenyl)ethyl]-3-chloro-1,3-dimethylcyclobutanecarboxamide;
[1(R)-trans]-3-bromo-N-[1-(4-bromophenyl)ethyl]-1,3-dimethylcyclobutanecarboxamide;
[1(R)-cis]-3-bromo-N-[1-(4-bromophenyl)ethyl]-1,3-dimethylcyclobutanecarboxamide;
[1(R)-trans]-3-chloro-N-[1-(2,4-dichlorophenyl)ethyl]-1,3-dimethylcyclobutanecarboxamide;
[1(R)-cis]-3-chloro-N-[1-(2,4-dichlorophenyl)ethyl]-1,3-dimethylcyclobutanecarboxamide;
[1(R)-cis]-N-[1-(4-bromo-2-methoxyphenyl)ethyl]-3-chloro-1,3-dimethylcyclobutanecarboxamide; and
[1(R)-cis]-N-[1-(4-bromophenyl)ethyl]-3-chloro-3-(chloromethyl)-1-methylcyclobutanecarboxamide.

Preferred 3
Compounds of Formula I above wherein
$R^1$ is halogen or $C_1$–$C_2$ alkyl;
$R^2$ is halogen or $C_1$–$C_2$ alkyl;
$R^3$ is hydrogen or $C_1$–$C_2$ alkyl optionally substituted with halogen;
$R^4$ is $CH_3$;
$R^5$ is $CH_2OR^6$; and
$R^6$ is phenyl optionally substituted with one to two substituents selected from the group halogen, $C_1$–$C_4$ alkyl, $C_1$–$C_4$ haloalkoxy and cyano.

Preferred 4
Most preferred compounds include compounds of Preferred 3 selected from the group

[1(R)-cis]-3-chloro-N-[2-(2-fluorophenoxy)-1-methylethyl]-3-methyl-1-(trifluoromethyl)cyclobutanecarboxamide;
[1(R)-trans]-3-chloro-N-[2-(2-fluorophenoxy)-1-methylethyl]-3-methyl-1-(trifluoromethyl)cyclobutanecarboxamide;
[1(R)-trans]-3-chloro-N-[2-(2-fluorophenoxy)-1-methylethyl]-3-methyl-1-(trifluoromethyl)cyclobutanecarboxamide;
[1(R)-trans]-3-chloro-N-[2-(2,5-difluorophenoxy)-1-methylethyl]-3-methyl-1-(trifluoromethyl)cyclobutanecarboxamide;
[1(R)-cis]-3-chloro-N-[2-(2,5-difluorophenoxy)-1-methylethyl]-1,3-dimethylcyclobutanecarboxamide;
[1(R)-cis]-3-chloro-N-[2-(5-chloro-2-cyanophenoxy)-1-methylethyl]-1,3-dimethylcyclobutanecarboxamide; and
[1(R)-cis]-3-chloro-N-[2-(2-cyano-5-fluorophenoxy)-1-methylethyl]-1,3-dimethylcyclobutanecarboxamide.

Preferred 5
Compounds of Formula I above wherein
$R^1$ is halogen or $C_1$–$C_2$ alkyl;
$R^2$ is halogen or $C_1$–$C_2$ alkyl; and
$R^3$ is $C_1$–$C_2$ alkyl optionally substituted with halogen;
$R^4$ is $CH_3$;
$R^5$ is $R^6$; and
$R^6$ is naphthalenyl optionally substituted with one to three substituents selected from the group halogen, $C_1$–$C_4$ alkyl, $C_1$–$C_4$ haloalkoxy and cyano.

Preferred 6
Most preferred compounds of Preferred 5 include [1(R)-cis]-3-chloro-1,3-dimethyl-N-[-(2-naphthalenyl)ethyl]cyclobutanecarboxamide.

Preferred mixtures include mixtures (e.g., a 1:1 molar mixture) of [1(R)-cis]-N-[1-(4-bromophenyl)ethyl]-3-chloro-3-methyl-1-(trifluoromethyl)cyclobutanecarboxamide with [1(R)-trans]-N-[1-(4-bromophenyl)ethyl]-3-chloro-3-methyl-1-(trifluoromethyl)cyclobutanecarboxamide. Preferred mixtures also include mixtures (e.g., a 1:1 molar mixture) of [1(R)-cis]-3-chloro-N-[2-(2-fluorophenoxy)-1-methylethyl]-3-methyl-1-(trifluoromethyl)cyclobutanecarboxamide with [1(R)-trans]-3-chloro-N-[2-(2-fluorophenoxy)-1-methylethyl]-3-methyl-1-(trifluoromethyl)cyclobutanecarboxamide.

Of note are compounds of Formula I where $R^1$ is halogen or $C_1$–$C_2$ alkyl. Also of note are compounds of Formula I were $R^2$ is halogen or $C_1$–$C_2$ alkyl. Further of note are compounds of Formula I were $R^6$ is phenyl optionally substituted with one to two substituents selected from the group halogen, $C_1$–$C_4$ alkyl, $CF_3$, $C_1$–$C_4$ haloalkoxy and cyano.

This invention also relates to fungicidal compositions comprising fungicidally effective amounts of the compounds of the invention and at least one of a surfactant, a solid diluent or a liquid diluent. The preferred compositions of the present invention are those which comprise the above preferred compounds.

This invention also relates to a method for controlling plant diseases caused by fungal plant pathogens comprising applying to the plant or portion thereof, to a flooded rice paddy, or to the plant seed or seedling, a fungicidally effective amount of the compounds of the invention (e.g., as a composition described herein). The preferred methods of use are those involving the above preferred compounds.

DETAILS OF THE SYNTHESIS

The compounds of Formula I can be prepared by one or more of the following methods and variations as described in Schemes 1–12. The definitions of X, $X^1$ and $R^1$–$R^{14}$ in the compounds of Formulae 1–20 below are as defined above in the Summary of the Invention or in the schemes below.

Scheme 1

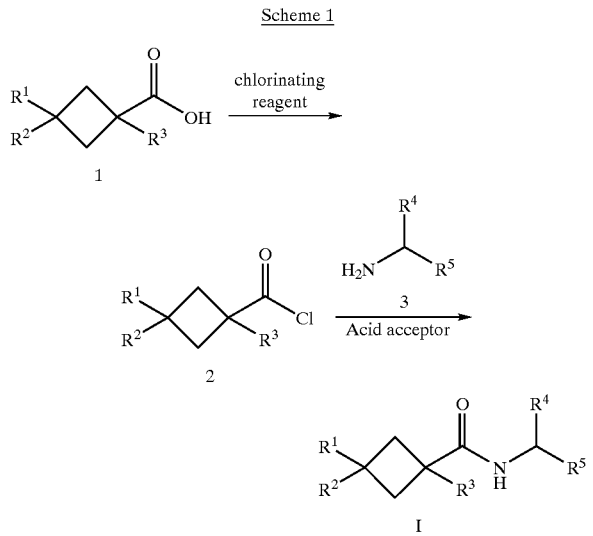

Cyclobutane carboxylic acids of Formula 1 are converted to the corresponding acid chlorides of Formula 2. This reaction can be carried out by using 1–10 equivalents of any of a variety of chlorinating reagents, such as thionyl chloride or oxalyl chloride, either neat or in insert solvent, over a wide temperature range. Examples of suitable solvents include dichloromethane, toluene and dichloroethane. Generally, the reaction is carried out at a temperature between 0° C. and the boiling point of the reaction mixture for 0.1 to 72 h. Optionally, promoters, such as N,N-dimethylformamide (DMF), can be used in conjunction with the chlorinating reagent. The acid chlorides are in turn reacted with an amine of Formula 3 to give the amide I. The process can be carried out over a wide temperature range in a wide variety of solvents. Generally, the reaction is carried out at a temperature between −30° C. and 60° C. for 0.1 to 72 h. Optionally, 1–10 equivalents of an acid acceptor, such as sodium carbonate or triethylamine, can be added to neutralize acid that is formed. The reaction can be done in an inert solvent, such as dichloromethane, toluene, tetrahydrofuran (THF), dioxane, or DMF, in water, or in a two component solvent mixture, such as 1:1 dioxane-water.

Scheme 2

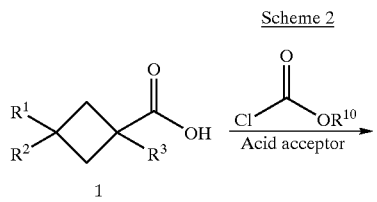

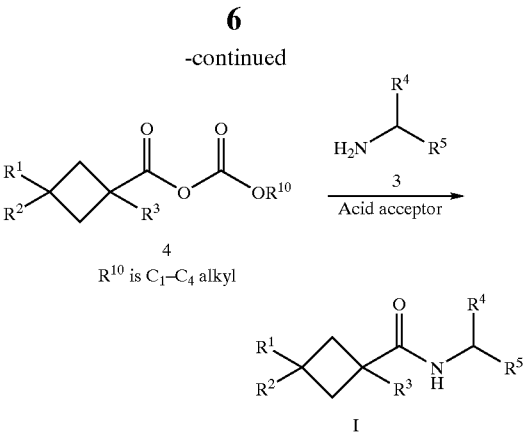

$R^{10}$ is $C_1$–$C_4$ alkyl

Cyclobutane carboxylic acids of Formula 1 are also converted to the corresponding mixed anhydrides of Formula 4. This reaction can be carried out by using 1–10 equivalents of a variety of carbonic acid derivatives, such as ethyl chloroformate or isobutyl chloroformate, in an inert solvent. Generally, the reaction is carried out at a temperature between −30° C. and 20° C. for 0.1 to 72 h. Often, the reaction is performed along with 1–10 equivalents of an acid acceptor, such as triethylamine or N-methyl morpholine, to neutralize acid that is formed. Examples of suitable solvents include dichloromethane, toluene, tetrahydrofuran (THF), dioxane, or DMF. The mixed anhydrides are in turn reacted with an amine of Formula 3 to give the amide I. The process can be carried out over a wide temperature range in a wide variety of solvents. Generally, the reaction is carried out at a temperature between −30° C. and 60° C. for 0.1 to 72 h. 1–10 Equivalents of an acid acceptor, such as triethylamine or N-methyl morpholine, are also often added to neutralize acid that is formed. The reaction can be done in any inert solvent such as dichloromethane, toluene, or dioxane.

Scheme 3

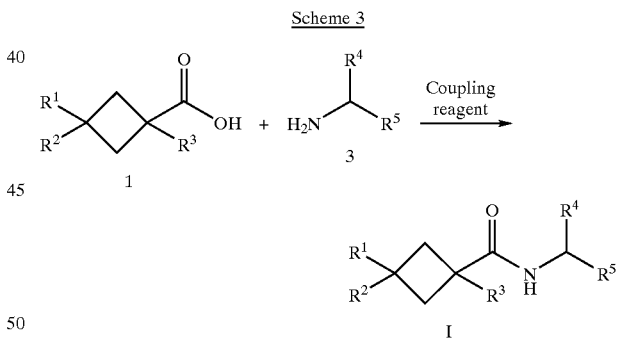

Cyclobutane carboxylic acids of Formula 1 can also be directly coupled with amines of Formula 3 in the presence of 1–10 equivalents of a coupling reagent such as dicyclohexylcarbodiimide (DCC), 1,1'-carbonyldiimidazole (CDI), 1,1'-carbonylbis[3-methyl-1H-imidazolium] (1:2) salt with trifluoromethanesulfonic acid (CBMIT) or, N'-(ethylcarbonimidoyl)-N,N-dimethyl-1,3-propanediamine monohydrochloride (EDCI). The process can be carried out over a wide temperature range in a wide variety of solvents. Generally, the reaction is carried out at a temperature between −30° C. and 20° C. for 0.1 to 72 h. The reaction can be done in any inert solvent such as dichloromethane, toluene, acetonitrile, or dioxane.

One skilled in the art will recognize that there are many other methods for the preparation of amides from carboxylic acids and amines which are not specified here. The intent of this part of the description of the invention is only to identify some potentially useful methods for the preparation of compounds of Formula I and is not intended to identify every possible method.

Cyclobutane carboxylic acids of Formula 1 are known or can be prepared by a variety of methods. The preparation of cyclobutane carboxylic acid of Formula 1 where $R^1$=Cl, $R^2$=$R^3$=H is disclosed in the literature (Hall, H. K.; Blanchard, E. P.; Cherkofsky, S. C.; Sieja, J. B.; and Sheppard, W. A. *J. Amer. Chem. Soc.* 1971, 93, 110–20). The preparation of cyclobutane carboxylic acid of Formula 1 where $R^1$=Cl, $R^2$=$CH_3$, and $R^3$=H is disclosed in the literature (Hall, H. K., Jr.; Smith, C. D.; Blanchard, E. P.; Cherkofsky, S. C.; and Sieja, J. B. *J. Amer. Chem. Soc.* 1971, 93, 121–9). The preparation of cyclobutane carboxylic acids of Formula 1 where $R^1$=Cl, $R^2$=$CH_3$ or H and $R^3$=$CH_3$ or $CF_3$ is disclosed in the literature (Hall, H. K., Jr.; Blanchard, E. P.; and Martin, E. L. *Macromolecules* 1971, 4, 142–6).

Scheme 4

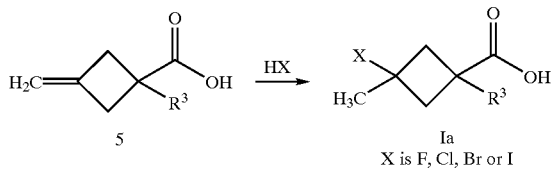

X is F, Cl, Br or I

Additional cyclobutane carboxylic acids of Formula 1a can be prepared by the addition of hydrohalogen acids to 3-methylene-1-cyclobutane carboxylic acids of Formula 5 (Scheme 4). This reaction can be carried out using any strong acid, such as hydrogen chloride or hydrogen bromide, over a wide temperature range. The strong acid used can be either as an aqueous solution or as a gas, either with or without solvent. The reaction can be done at atmospheric pressure or under pressure in a sealed reaction vessel. Generally, the reaction is carried out at a temperature between 20° C. and the reflux temperature of the mixture using a concentrated aqueous solution of the acid for 0.1 to 72 h. Any solvent that is not reactive to strong acid is suitable, examples being water, methanol, ethanol, or dioxane.

Scheme 5

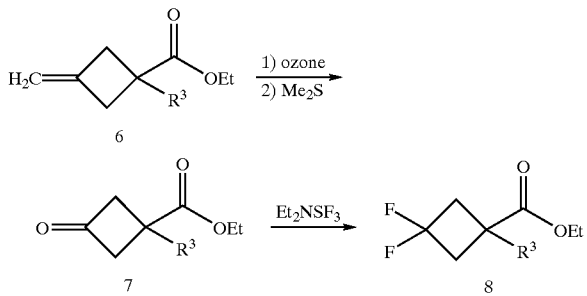

Cyclobutane carboxylic esters of Formula 8 can be prepared by the addition of two molecules of fluorine to ketone intermediate of Formula 7. This transformation can be done with a number of different fluorinating reagents, such as (diethylamino)sulfur trifluoride (DAST), over a wide temperature range. Generally, the reaction is carried out at a temperature between −40° C. and ambient temperature, in an inert solvent, such as dichloromethane, 1,2-dichloroethane, or toluene. Intermediate of Formula 7 can be formed by the treatment of intermediate of Formula 6 with ozone, followed by treatment with of the solution with a reducing reagent, such as dimethylsulfide. This reaction can be carried out in any convenient solvent that is not subject to ozone oxidation, such as dichloromethane, 1,2-dichloroethane, or toluene, at a temperature between −90 to −60° C.

Scheme 6

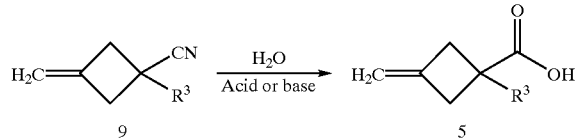

3-Methylene-1-cyclobutane carboxylic acids of Formula 5 can be prepared by the hydrolysis of the corresponding cyclobutane carbonitrile of Formula 9 (Scheme 6). This reaction can be carried out by using aqueous hydroxide solution or by any strong aqueous acid, such as hydrogen chloride or hydrogen bromide, over a wide temperature range. Generally, the reaction is carried out at a temperature between 20° C. and the reflux temperature of the mixture for 0.1 to 72 h. The reaction can be done at atmospheric pressure or under high pressure in a sealed reaction vessel. Generally, hydrolysis using base is done at atmospheric pressure at the boiling point of the mixture and hydrolysis with acid is done at 100° C. in a sealed reaction vessel. Hydrolysis using aqueous hydrohalogenic acid will give the cyclobutane carboxylic acid of Formula 1a directly.

Scheme 7

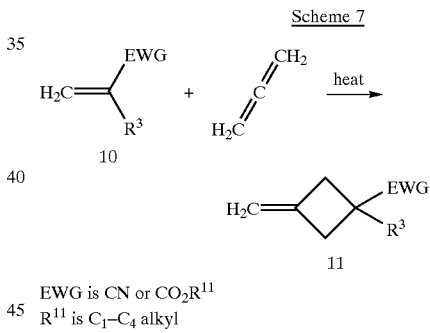

EWG is CN or $CO_2R^{11}$
$R^{11}$ is $C_1$–$C_4$ alkyl

3-Methylene-1-cyclobutane carbonitriles and esters of Formula 11 can be prepared by the thermal cycloaddition of allene to the appropriately substituted acrylonitrile or acrylate ester of Formula 10 (Scheme 7). This reaction can be carried out under pressure in a sealed reaction vessel over a wide temperature range. Generally, the reaction is carried out at a temperature above 100° C. in a pressurized reaction vessel for 0.5 to 72 h with 1–100 equivalents of allene. Optionally, an inert solvent, such as benzene, can be used. Optionally, 0.0 1–1 equivalent of some polymerization inhibitor, such a hydroquinone or 4-methoxyphenol, can be used. Appropriately substituted acrylonitriles or acrylate esters of Formula 10 are commercially available or known in the literature. For example, the preparation of ethyl α-fluoromethyl-acrylate is reported by Powell and Graham (*J. Polymer Sci.* Part A, 1965, 3, 3451–8).

Amines of Formula 3 are known or can be prepared by a variety of methods. Amines of Formula 3 where $R^4$=$CH_3$, $R^5$=$R^6$ and $R^6$=phenyl, 4-chlorophenyl, 4-bromophenyl 1-naphthyl, or 2-naphthyl are commercially available. Additional amines of Formula 3 can be prepared from the corresponding ketones or aldehydes by reductive amination (Borch reduction) as shown in Scheme 8.

Scheme 8

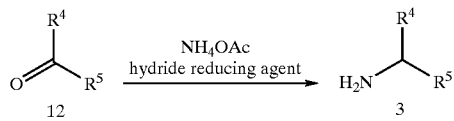

$R^5$ is $R^6$ wherein $R^6$ is other than substituted pyrrole, $CH(R^8)OR^6$, $CH(R^8)CH(R^7)R^6$ or $C(R^8)=C(R^7)R^6$ wherein $R^6$ is other than substituted pyrrole $R^6$ is

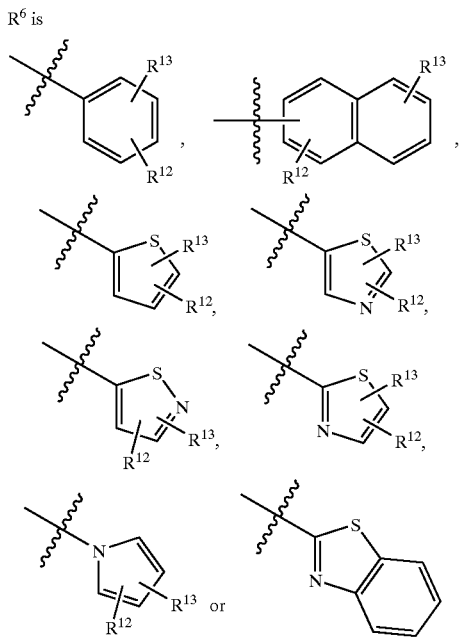

$R^{12}$ and $R^{13}$ are each independently hydrogen, halogen, $C_1$–$C_4$ alkyl, $C_1$–$C_4$ haloalkyl, $C_1$–$C_4$ alkoxy, $C_1$–$C_4$ haloalkoxy, $Si(CH_3)_3$, cyano, $NHC(=O)R^9$ or $NHC(=S)R^9$ The reductive amination can be carried out using 1–10 equivalents of an ammonium halide or acetate salt, such as ammonium acetate, and 1–10 equivalents of a hydride reducing agent, such as sodium cyanoborohydride. The reaction can be run in any suitable solvent, such as methanol, ethanol, THF or dichloromethane. Optionally, an acid, such as HCl or p-toluenesulfonic acid, can be added portionwise during the course of the reaction so as to maintain a pH of 3–5. Typical temperatures for the reductive amination range from −5° C. to 60° C. Acetyl substituted benzenes (acetophenones) and acetyl substituted heterocycles are known and many are commercially available.

Scheme 9

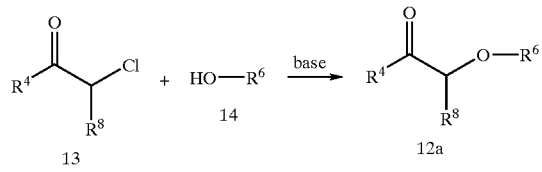

Compounds of Formula 12a can be prepared by the alkylation of variously substituted compounds of Formula 14 with α-chloro ketones of Formula 13 (Scheme 9). This reaction may be done over a wide variety of temperatures in a range of solvents. Generally, the reaction is performed at temperatures ranging from 20° C. to the boiling point of the mixture. Optionally, 1–10 equivalents of an acid acceptor, such as potassium carbonate or triethylamine, is added to neutralize acid that is formed. Suitable solvents include acetone, methyl ethyl ketone, THF, DMF, or water.

Scheme 10

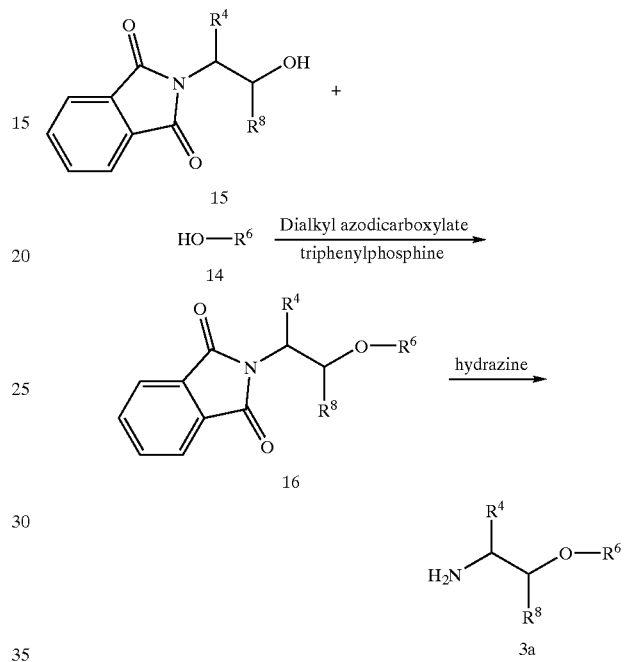

A method of synthesis of amines of Formula 3a is reaction of the corresponding phthalimides of Formula 16 with hydrazine (Scheme 10). The phthalimides of Formula 16 are prepared in turn from hydroxy phthalimides of Formula 15 and the appropriately substituted compound of Formula 14 in the presence of 1–2 equivalents of triphenylphosphine and 1–2 equivalents of a dialkyl azodicarboxylate, such as diethyl azodicarboxylate (DEAD). The reaction is generally run in an inert solvent such as dicloromethane or THF at a temperature range between −30° C. and the boiling point of the mixture. The resulting phthalimides of Formula 16 are converted to the amines of Formula 3a by the reaction of 1–10 equivalents hydrazine or some other primary amine. This reaction is generally run in a polar solvent, such as ethanol or THF, at a temperature range of between 20° C. and the boiling point of the mixture.

Scheme 11

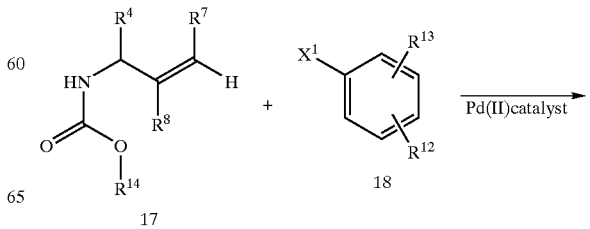

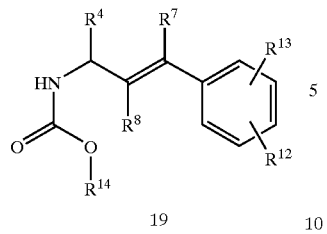

19

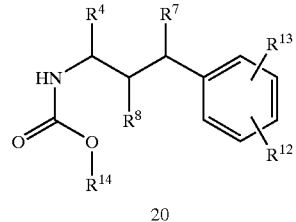

20

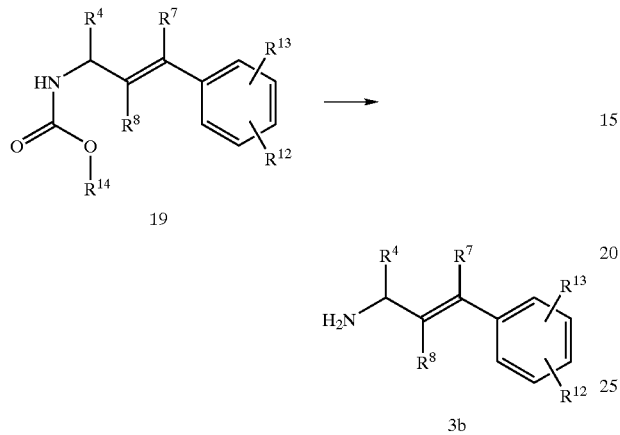

$R^{14}$ is $C_1$–$C_4$ alkyl or benzyl
$X^1$ is Br or I

The amines of Formula 3b can be prepared by hydrolysis of the corresponding carbamates of Formula 19 (Scheme 11). These carbamates can in turn be made by coupling a suitably protected allylic amines of Formula 17 with aromatic bromides of iodides of Formula 18. Appropriate catalysts for the coupling reaction (Heck reaction) include $PdCl_2$ and $Pd(OAc)_2$ complexed with 2–4 fold excess phosphine ligand such as triphenylphosphine. Typically 1–10 mol % of the appropriate catalyst is used. The reactions are performed between 0° C. and 100° C. with 1–3 equivalents of base, such as potassium carbonate or triethylamine. Often 10–50 mol % of a phase transfer catalyst, such as tetrabutylammonium bromide, is used in the reaction mixture. Typical solvents include acetonitrile and DMF. Carbamates of Formula 19 wherein $R^{14}$ is typically t-butyl or benzyl are removed by standard methods set out in the literature (see Greene, T. W.; Wuts, P. G. M. *Protective Groups in Organic Synthesis*, 2nd ed.; Wiley: New York, 1991).

Scheme 12

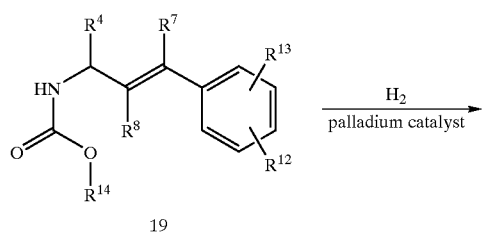

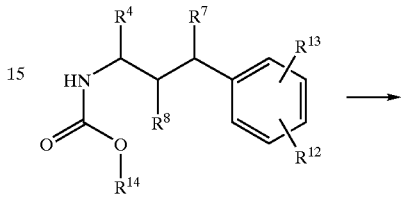

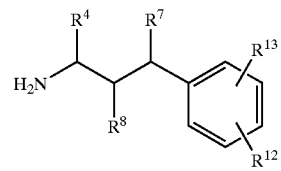

Amines of Formula 3c are available from the corresponding carbamates of Formula 20 which are in turn accessible from the allylic carbamates of Formula 19 (Scheme 12). Reduction of the allylic carbamate is conveniently done by hydrogenation in the presence of a metal catalyst, such as 5% palladium impregnated on carbon. This reduction can be carried out over a wide temperature range in a variety of solvents under pressure of hydrogen gas. Generally hydrogenations are carried out at 20° C. under 30 psi of hydrogen. Any solvent compatible with hydrogenation is suitable, for example THF, methanol, ethanol, or water. Carbamates of Formula 20 wherein $R^{14}$ is typically t-butyl or benzyl are removed by standard methods set out in the literature (see Greene, T. W.; Wuts, P. G. M. *Protective Groups in Organic Synthesis*, 2nd ed.; Wiley: New York, 1991). Hydrogenation of the carbamate of Formula 19 where $R^{14}$ is benzyl will simultaneously reduce the double bond and remove the carbamate functional group to give the amine of Formula 3c directly.

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s=singlet, d=doublet, t=triplet, q=quartet, m=multiplet, dd=doublet of doublets and br s=broad singlet. Coupling constants are indicated by J and reported in Hertz.

EXAMPLE 1

Preparation of (R)-3-chloro-N-[1-(4-chlorophenyl) ethyl]-3-methyl-1-(trifluoromethyl) cyclobutanecarboxamide A solution of 0.240 g (1.11 mmol) of 3-chloro-3-methyl-1-(trifluoromethyl)cyclobutane carboxylic acid (prepared according to the method described by H. K. Hall, Jr., E. P. Blanchard Jr. and E. L Martin in *Macromolecules* 4(2) 142–146 (1971)) in 5 mL thionyl chloride was heated at reflux for 1 h. Solvent was removed in vacuo. The residue was added to a solution of 0.176 g (1.66 mmol) sodium carbonate and 0.172 g (1.11 mmol) (R)-4-chloro-α-methylbenzenemethanamine in 6 mL of 1:1 dioxane-water, pre-cooled to 0° C. After stirring at room temperature overnight, the mixture was poured into 50 mL water and extracted two times with 50 mL ethyl acetate (EtOAc). Drying (magnesium sulfate) and removal of the solvent gave an oil which was chromatographed on silica gel, eluting with 25% hexane-dichloromethane, to afford 43 mg of the cis isomer of the title compound: mp 129–130° C., $^1$H NMR (CDCl$_3$) δ1.49 (d, 3H), 1.69 (s, 3H), 2.86–2.95 (m, 2H), 2.98–3.05 (m, 2H), 5.05–5.12 (q, 1H), 5.86 (s, 1H), 7.20 (d, 2H), 7.32 (d, 2H), and 77 mg of the trans isomer of the title compound: mp 145–146 C, $^1$H NMR (CDCl$_3$) 1.54 (d, 3H), 1.74 (s, 3H), 1.74 (s, 3H), 2.79–2.86 (m, 2H), 3.13 (d, 2H), 5.14 (q, 1H), 5.85 (s, 1H), 7.23 (d, 2H), 7.31 (d, 2H).

EXAMPLE 2

Step A

Preparation of (R)-2-[2-(2,5-difluorophenoxy)-1-methylethyl]-1H-isoindole-1,3(2H)-dione (R)-2-(2-Hydroxy-1-methylethyl)-1H-isoindole 1,3(2H)-dione (Becker, Y. J. *J. Org. Chem.* 1980, 45, 2145–51) was diluted with 40 mL THF then treated in order with 7.0 g triphenyl phosphine, 4.0 g of 2,5-difluorophenol and finally with 5.0 mL of diethylazocarboxylate. The reaction became warm to the point of reflux and was allowed to cool to room temperature and stirred at room temperature overnight. The solvent was removed in vacuo and the resulting brown oil was taken up in ethyl acetate (EtOAc). The solution was washed sequentially with aqueous sodium bicarbonate, aqueous ammonium chloride, and brine. Removal of the solvent gave an oil which was chromatographed on silica gel, eluting with 10% ethyl acetate-hexane, to afford 5.4 g of the title compound of Step A as a clear colorless oil: $^1$H NMR (CDCl$_3$) δ1.57 (d, 3H), 4.22 (dd, 1H), 4.57 (t, 1H), 4.82 (m, 1H), 6.55 (m, 1H), 6.70 (m, 1H), 6.95 (m, 1H), 7.72 (m, 2H), 7.82 (m, 2H).

Step B

Preparation of (R)-1-(2,5-difluorophenoxy)-2-propanamine hydrochloride

To 5.4 g (R)-2-[2-(2,5-difluorophenoxy)-1-methylethyl]-1H-isoindole-1,3(2H)-dione in 250 mL absolute ethanol was added 6.0 mL hydrazine. The solution was heated to reflux for 100 minutes. A white precipitate formed. The reaction was allowed to cool to room temperature and was filtered to remove the precipitate. Concentration of the filtrate gave a gummy paste which was taken up in ethyl acetate and washed once with brine and twice with 100 mL 1N hydrochloric acid. The combined acidic aqueous layers were basified with 1N sodium hydroxide and extracted three times with ethyl acetate. The combined organic extracts were dried and the solvent was removed to afford an oil. The oil was diluted with dry ether and 30 mL of 1N hydrochloric acid in ether was added. The resulting white precipitate was collected by filtration and dried to give the title compound of Step B as a white powder: mp 127–130° C., $^1$H NMR (Me$_2$SO-d$_6$) δ1.30 (d, 3H), 3.60 (m, 1H), 4.22 (m, 2H), 6.80 (m, 1H), 7.22 (m, 2H), 8.30 (br s, 3H).

Step C

Preparation of 3-chloro-1,3-dimethylcyclobutanecarboxylic acid

To 3.0 g (0.028 mole) of 1-methyl-3-methylenecyclobutanecarbonitrile (prepared according to the method described by H. K. Hall, Jr., E. P. Blanchard Jr. and E. L Martin in *Macromolecules* 4(2) 142–146 (1971)) there was added 50 ML of 1 N sodium hydroxide and 12 pellets of sodium hydroxide. The mixture was refluxed with stirring for 5 hours, during which the nitrile went into solution. The reaction mixture was cooled to room temperature and extracted with 50 mL of diethyl ether. The aqueous layer was acidified to pH 0 with concentrated hydrochloric acid and then extracted twice with 50 mL of dichloromethane. The combined organic layers were dried over sodium sulfate, filtered and the solvent removed in vacuo giving 3.17 g of a colorless oil. This oil was added with vigorous stirring to 50 mL of concentrated hydrochloric acid (37%) at room temperature over five minutes and then stirred for one hour longer. The white crystalline solid that separated was extracted with 100 mL of dichloromethane. The organic layer was dried over sodium sulfate, filtered, and the solvent removed in vacuo giving 3.3 g of a white solid that was shown by $^1$H NMR to be a mixture of the cis and trans diastereomers (unassigned) of the title compound of Step C in a ratio of approximately 1.3:1. $^1$H NMR (Me$_2$SO-d$_6$) δ1.33 (s, 3H), 1.47 (s, 3H), 1.65 (s, 3H), 1.73 (s, 3H), 2.33 (d, 2H), 2.43 (d, 2H), 2.50 (d, 2H), 2.83 (d, 2H), 2.94 (d, 2H), 12.45 (s, 1H).

Step D

Preparation of (R)-3-chloro-N-[2-(2,5-difluorophenoxy)-1-methylethyl]-3-methyl-1-(trifluoromethyl)cyclobutanecarboxamide Under nitrogen, 3-chloro-1,3-dimethylcyclobutanecarboxylic acid (0.98 g, 0.006 mole) was stirred with 5 mL (excess) thionyl chloride and two drops of N,N-dimethylforamide as catalyst overnight or until the gas evolution ceased. The excess thionyl chloride was removed in vacuo, 10 mL of benzene added and the solvent again removed in vacuo. Under nitrogen, the residual acid chloride (0.005 mole) in 25 mL of dichloromethane was added dropwise over approximately 10 minutes to a solution of 1.12 (0.005 mole) of (R)-1-(2,5-difluorophenoxy)-2-propanamine hydrochloride, 1.0 g (0.1 mole) of triethylamine and a catalytic amount of 4-dimethyaminopyridine in 50 mL of dichloromethane. An exotherm to 26° C. was noted. The reaction mixture was then stirred at room temperature for two hours 15 minutes and then 50 mL of dichloromethane was added. The organic layer was washed with 100 mL of 1 N hydrochloric acid, and then with 100 mL of 0.5 N sodium hydroxide. The organic layer was then dried over sodium sulfate, filtered, and the solvent removed in vacuo giving 1.16 g of an amber oil. Thin layer chromatography in 1:1 diethyl ether:hexanes showed two major spots with $R_f$ of 0.3 and 0.2. The diastereomers were separated by flash chromatography on 120 g of silica gel eluting with 1:1 diethyl ether:hexanes to afford 600 mg of the trans isomer of the title compound of Step D as an oil, $^1$H NMR (Me$_2$SO-d$_6$) δ1.14 (d, 3H), 1.42 (s, 3H), 1.52 (s, 3H), 2.38 (m, 2H), 2.82 (m, 2H), 3.99 (d, 2H), 4.15 (m, 1H), 6.70 (m, 1H), 7.19 (m, 2H), 7.67 (d, 1H) and 300 mg of the cis isomer of the title compound of Step D as an oil, $^1$H NMR (Me$_2$SO-d$_6$) δ1.30 (s, 3H), 1.58 (d, 3H), 1.72 (s, 3H), 2.27 (m, 2H), 2.93 (m, 2H), 3.99 (m, 2H), 4.15 (m, 1H), 6.70 (m, 1H), 7.18 (m, 2H), 7.61 (d, 1H).

EXAMPLE 3

Step A

Preparation of 3,3-difluoro-1-methylcyclobutanecarboxylic acid

Ethyl 1-methyl-3-methylenecyclobutanecarboxylate (3.0 g, 19 mmol) (prepared according to the method described by H. K. Hall, Jr., E. P. Blanchard, Jr. And E. L. Martin in *Macromolecules* 4(2) 142–146 (1971)) was dissolved in CH$_2$Cl$_2$ (150 mL) at –78° C. Ozone from an ozone generator was bubbled through the solution while stirring for 30 minutes, upon which the reaction mixture turned blue. Oxygen was bubbled though the solution followed by N$_2$, until the blue color disappeared. Dimethyl sulfide (4.3 mL, 58 mmol) was added to the clear solution and the mixture was stirred overnight at room temperature. The reaction mixture was washed with H$_2$O, dried (MgSO$_4$), and evaporated in vacuo to yield the corresponding ketone as a yellow oil (3.2 g, 93%). The resulting ketone (0.50 g, 2.97 mmol) in CH$_2$Cl$_2$ (15 mL) under N$_2$ was treated with DAST (1.15 mL, 8.92 mmol) and stirred overnight at room temperature. The reaction mixture was poured over ice and extracted with CH$_2$Cl$_2$, dried (MgSO$_4$) and evaporated in vacuo to yield the corresponding difluoro ester as an orange oil (0.40 g, 76%). Saponification of the ester provided the title compound as a brown oil quantitatively: $^1$H NMR (CDCl$_3$, 300 MHz) δ1.53 (s, 3H), 2.47 (m, 2H), 3.09 (m, 2H); $^{19}$F NMR (CDCl$_3$, 282 MHz) δ–92.5 (d), –88.2 (d).

Step B

Preparation of (R)-N-[1-(4-bromophenyl)ethyl]-3,3-difluoro-1-methylcyclobutanecarboxamide To 3,3-difluoro-1-methylcyclobutanecarboxylic acid (0.30 g, 2.0 mmol) in CH$_2$Cl$_2$ (8 ml) under N$_2$ was added 1 drop DMF and oxalyl chloride (0.21 mL, 2.4 mmol). The mixture was stirred overnight at room temperature under N$_2$. A solution of R-(+)-4-bromophenylethylamine hydrochloride (0.47 g, 2.0 mmol) and triethylamine (0.61 mL, 4.4 mmol) in CH$_2$Cl$_2$ (5 mL) was added to the reaction mixture and stirring was continued overnight at room temperature. The reaction mixture was diluted with CH$_2$Cl$_2$ and washed with water, 1N HCl and 1N NaOH. The organic phase was dried (MgSO$_4$) and evaporated in vacuo to yield the title compound as an orange solid (0.49 g, 74%): mp 120–122° C.; $^1$H NMR (CDCl$_3$, 300 MHz) δ1.48 (d, J=7.2 Hz, 3H), 1.58 (s, 3H), 2.40 (m, 2H), 3.01 (m, 2H), 5.06 (m, 1H), 5.66 (d, J=7.2 Hz, 1H), 7.17 (d, J=8.1 Hz, 2H), 7.47 (d, J=8.1 Hz, 2H); $^{19}$F NMR (CDCl$_3$, 282 MHz) δ–93.3 (d), –87.4 (d).

By the procedures described herein together with methods known in the art, the following compounds of Tables 1 to 9 can be prepared. The following abbreviations are used in the Tables which follow: t=tertiary, s=secondary, n=normal, i=iso, Me=methyl, Et=ethyl, Pr=propyl, i-Pr=isopropyl, Bu=butyl, n-Bu=normal-butyl, t-Bu=tert-butyl, Ph=phenyl, pyr=pyridinyl, OMe=methoxy, and CN=cyano.

TABLE 1

| $R^1$ | $R^3$ | $R^{13}$ | $R^{12}$ |
|---|---|---|---|
| | | Column 1 | |
| H | Me | Cl | 4-Me |
| H | Me | Cl | 4-Cl |
| H | Me | Cl | 4-Br |
| H | Me | Cl | 4-I |
| H | Me | Cl | 4-CF$_3$ |
| H | Me | Br | 4-Me |
| H | Me | Br | 4-Cl |
| H | Me | Br | 4-Br |
| H | Me | Br | 4-I |
| H | Me | Br | 4-CF$_3$ |
| H | Me | I | 4-Me |
| H | Me | I | 4-Cl |
| H | Me | I | 4-Br |
| H | Me | I | 4-I |
| H | Me | I | 4-CF$_3$ |
| Cl | Me | H | 4-Me |
| Cl | Me | H | 4-Cl |
| Cl | Me | H | 4-Br |
| Cl | Me | H | 4-I |
| Cl | Me | H | 4-CF$_3$ |
| Cl | Me | Cl | 4-Me |
| Cl | Me | Cl | 4-Cl |
| Cl | Me | Cl | 4-Br |
| Cl | Me | Cl | 4-I |
| Cl | Me | Cl | 4-CF$_3$ |
| Cl | Me | OMe | 4-Me |
| Cl | Me | OMe | 4-Cl |
| Cl | Me | OMe | 4-Br |
| Cl | Me | OMe | 4-F |
| Cl | Me | OMe | 4-CF$_3$ |
| Cl | Me | Br | 4-Me |
| Cl | Me | Br | 4-Cl |
| Cl | Me | Br | 4-Br |
| Cl | Me | Br | 4-I |
| Cl | Me | Br | 4-CF$_3$ |
| Cl | Me | I | 4-Me |
| Cl | Me | I | 4-Cl |
| Cl | Me | I | 4-Br |
| Cl | Me | I | 4-I |
| Cl | Me | I | 4-CF$_3$ |
| Br | Me | H | 4-Me |

TABLE 1-continued

| R¹ | R³ | R¹³ | R¹² |
|---|---|---|---|
| Br | Me | H | 4-Cl |
| Br | Me | H | 4-Br |
| Br | Me | H | 4-I |
| Br | Me | H | 4-CF₃ |
| Br | Me | Cl | 4-Me |
| Br | Me | Cl | 4-Cl |
| Br | Me | Cl | 4-Br |
| Br | Me | Cl | 4-I |
| Br | Me | Cl | 4-CF₃ |
| Cl | CH₂F | H | 4-Me |
| Cl | CH₂F | H | 4-Cl |
| Cl | CH₂F | H | 4-Br |
| Cl | CH₂F | H | 4-I |
| Cl | CH₂F | H | 4-CF₃ |
| Cl | CH₂F | Cl | 4-Me |
| Cl | CH₂F | Cl | 4-Cl |
| Cl | CH₂F | Cl | 4-Br |
| Cl | CH₂F | Cl | 4-I |
| Cl | CH₂F | Cl | 4-CF₃ |
| Cl | CH₂F | Br | 4-Me |
| Cl | CH₂F | Br | 4-Cl |
| Cl | CH₂F | Br | 4-Br |
| Cl | CH₂F | Br | 4-I |
| Cl | CH₂F | Br | 4-CF₃ |
| Cl | CH₂F | I | 4-Me |
| Cl | CH₂F | I | 4-Cl |
| Cl | CH₂F | I | 4-Br |
| Cl | CH₂F | I | 4-I |
| Cl | CH₂F | I | 4-CF₃ |
| Cl | CHF₂ | H | 4-Me |
| Cl | CHF₂ | H | 4-Cl |
| Cl | CHF₂ | H | 4-Br |
| Cl | CHF₂ | H | 4-I |
| Cl | CHF₂ | H | 4-CF₃ |
| Cl | CHF₂ | Cl | 4-Me |
| Cl | CHF₂ | Cl | 4-Cl |
| Cl | CHF₂ | Cl | 4-Br |
| Cl | CHF₂ | Cl | 4-I |
| Cl | CHF₂ | Cl | 4-CF₃ |
| Cl | CF₃ | H | 4-Me |
| Cl | CF₃ | H | 4-Cl |
| Cl | CF₃ | H | 4-Br |
| Cl | CF₃ | H | 4-I |
| Cl | CF₃ | H | 4-CF₃ |
| Cl | CF₃ | Cl | 4-Me |
| Cl | CF₃ | Cl | 4-Cl |
| Cl | CF₃ | Cl | 4-Br |
| Cl | CF₃ | Cl | 4-I |
| Cl | CF₃ | Cl | 4-CF₃ |
| Cl | CF₃ | CN | 4-Me |
| Cl | CF₃ | CN | 4-Cl |
| Cl | CF₃ | CN | 4-Br |
| Cl | CF₃ | CN | 4-I |
| Cl | CF₃ | CN | 4-CF₃ |
| Cl | CF₃ | NHCHO | 4-Me |
| Cl | CF₃ | NHCHO | 4-Cl |
| Cl | CF₃ | NHCHO | 4-Br |
| Cl | CF₃ | NHCHO | 4-I |
| Cl | CF₃ | NHCHO | 4-CF₃ |
| Cl | CF₃ | NHCOCH₃ | 4-Me |
| Cl | CF₃ | NHCOCH₃ | 4-Cl |
| Cl | CF₃ | NHCOCH₃ | 4-Br |
| Cl | CF₃ | NHCOCH₃ | 4-I |
| Cl | CF₃ | NHCOCH₃ | 4-CF₃ |
| Cl | Et | H | 4-Me |
| Cl | Et | H | 4-Cl |
| Cl | Et | H | 4-Br |
| Cl | Et | H | 4-I |
| Cl | Et | H | 4-CF₃ |
| Cl | Et | Cl | 4-Me |
| Cl | Et | Cl | 4-Cl |
| Cl | Et | Cl | 4-Br |
| Cl | Et | Cl | 4-I |
| Cl | Et | Cl | 4-CF₃ |
| Cl | Et | Br | 4-Me |
| Cl | Et | Br | 4-Cl |
| Cl | Et | Br | 4-Br |
| Cl | Et | Br | 4-I |
| Cl | Et | Br | 4-CF₃ |
| Cl | Et | I | 4-Me |
| Cl | Et | I | 4-Cl |
| Cl | Et | I | 4-Br |
| Cl | Et | I | 4-I |
| Cl | Et | I | 4-CF₃ |
| Cl | Cl | H | 4-Me |
| Cl | Cl | H | 4-Cl |
| Cl | Cl | H | 4-Br |
| Cl | Cl | H | 4-I |
| Cl | Cl | H | 4-CF₃ |
| Cl | Cl | Cl | 4-Me |
| Cl | Cl | Cl | 4-Cl |
| Cl | Cl | Cl | 4-Br |
| Cl | Cl | Cl | 4-I |
| Cl | Cl | Cl | 4-CF₃ |
| CH₂Cl | Me | H | 4-Me |
| CH₂Cl | Me | H | 4-Cl |
| CH₂Cl | Me | H | 4-Br |
| CH₂Cl | Me | H | 4-F |
| CH₂Cl | Me | H | 4-CF₃ |
| OMe | Me | H | 4-Me |
| OMe | Me | H | 4-Cl |
| OMe | Me | H | 4-Br |
| OMe | Me | H | 4-I |
| OMe | Me | H | 4-CF₃ |
| OMe | Me | Cl | 4-Me |
| OMe | Me | Cl | 4-Cl |
| OMe | Me | Cl | 4-Br |
| OMe | Me | Cl | 4-I |
| OMe | Me | Cl | 4-CF₃ |
| OCHF₂ | Me | H | 4-Me |
| OCHF₂ | Me | H | 4-Cl |
| OCHF₂ | Me | H | 4-Br |
| OCHF₂ | Me | H | 4-I |
| OCHF₂ | Me | H | 4-CF₃ |
| OCHF₂ | Me | Cl | 4-Me |
| OCHF₂ | Me | Cl | 4-Cl |
| OCHF₂ | Me | Cl | 4-Br |
| OCHF₂ | Me | Cl | 4-I |
| OCHF₂ | Me | Cl | 4-CF₃ |

Column 2

| R¹ | R³ | R¹³ | R¹² |
|---|---|---|---|
| H | Me | Cl | 4-Et |
| H | Me | Cl | 4-i-Pr |
| H | Me | Cl | 4-t-Bu |
| H | Me | Cl | 3-t-Bu |
| H | Me | Cl | 4-OCHF₂ |
| H | Me | Br | 4-Et |
| H | Me | Br | 4-i-Pr |
| H | Me | Br | 4-t-Bu |
| H | Me | Br | 3-t-Bu |
| H | Me | Br | 4-OCHF₂ |
| H | Me | I | 4-Et |
| H | Me | I | 4-i-Pr |
| H | Me | I | 4-t-Bu |
| H | Me | I | 3-t-Bu |
| H | Me | I | 4-OCHF₂ |

TABLE 1-continued

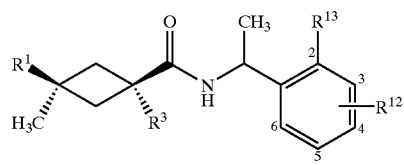

| R¹ | R³ | R¹³ | R¹² |
|---|---|---|---|
| Cl | Me | H | 4-Et |
| Cl | Me | H | 4-i-Pr |
| Cl | Me | H | 4-t-Bu |
| Cl | Me | H | 3-t-Bu |
| Cl | Me | H | 4-OCHF₂ |
| Cl | Me | Cl | 4-Et |
| Cl | Me | Cl | 4-i-Pr |
| Cl | Me | Cl | 4-t-Bu |
| Cl | Me | Cl | 3-t-Bu |
| Cl | Me | Cl | 4-OCHF₂ |
| Cl | Me | OMe | 4-Et |
| Cl | Me | OMe | 4-i-Pr |
| Cl | Me | OMe | 4-t-Bu |
| Cl | Me | OMe | 3-t-Bu |
| Cl | Me | OMe | 4-OCHF₂ |
| Cl | Me | Br | 4-Et |
| Cl | Me | Br | 4-i-Pr |
| Cl | Me | Br | 4-t-Bu |
| Cl | Me | Br | 3-t-Bu |
| Cl | Me | Br | 4-OCHF₂ |
| Cl | Me | I | 4-Et |
| Cl | Me | I | 4-i-Pr |
| Cl | Me | I | 4-t-Bu |
| Cl | Me | I | 3-t-Bu |
| Cl | Me | I | 4-OCHF₂ |
| Br | Me | H | 4-Et |
| Br | Me | H | 4-i-Pr |
| Br | Me | H | 4-t-Bu |
| Br | Me | H | 3-t-Bu |
| Br | Me | H | 4-OCHF₂ |
| Br | Me | Cl | 4-Et |
| Br | Me | Cl | 4-i-Pr |
| Br | Me | Cl | 4-t-Bu |
| Br | Me | Cl | 3-t-Bu |
| Br | Me | Cl | 4-OCHF₂ |
| Cl | CH₂F | H | 4-Et |
| Cl | CH₂F | H | 4-i-Pr |
| Cl | CH₂F | H | 4-t-Bu |
| Cl | CH₂F | H | 3-t-Bu |
| Cl | CH₂F | H | 4-OCHF₂ |
| Cl | CH₂F | Cl | 4-Et |
| Cl | CH₂F | Cl | 4-i-Pr |
| Cl | CH₂F | Cl | 4-t-Bu |
| Cl | CH₂F | Cl | 3-t-Bu |
| Cl | CH₂F | Cl | 4-OCHF₂ |
| Cl | CH₂F | Br | 4-Et |
| Cl | CH₂F | Br | 4-i-Pr |
| Cl | CH₂F | Br | 4-t-Bu |
| Cl | CH₂F | Br | 3-t-Bu |
| Cl | CH₂F | Br | 4-OCHF₂ |
| Cl | CH₂F | I | 4-Et |
| Cl | CH₂F | I | 4-i-Pr |
| Cl | CH₂F | I | 4-t-Bu |
| Cl | CH₂F | I | 3-t-Bu |
| Cl | CH₂F | I | 4-OCHF₂ |
| Cl | CHF₂ | H | 4-Et |
| Cl | CHF₂ | H | 4-i-Pr |
| Cl | CHF₂ | H | 4-t-Bu |
| Cl | CHF₂ | H | 3-t-Bu |
| Cl | CHF₂ | H | 4-OCHF₂ |
| Cl | CHF₂ | Cl | 4-Et |
| Cl | CHF₂ | Cl | 4-i-Pr |
| Cl | CHF₂ | Cl | 4-t-Bu |
| Cl | CHF₂ | Cl | 3-t-Bu |
| Cl | CHF₂ | Cl | 4-OCHF₂ |
| Cl | CF₃ | H | 4-Et |
| Cl | CF₃ | H | 4-i-Pr |
| Cl | CF₃ | H | 4-t-Bu |

TABLE 1-continued

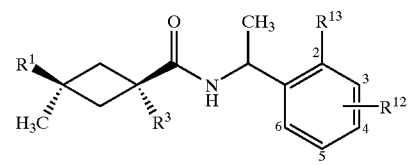

| R¹ | R³ | R¹³ | R¹² |
|---|---|---|---|
| Cl | CF₃ | H | 3-t-Bu |
| Cl | CF₃ | H | 4-OCHF₂ |
| Cl | CF₃ | Cl | 4-Et |
| Cl | CF₃ | Cl | 4-i-Pr |
| Cl | CF₃ | Cl | 4-t-Bu |
| Cl | CF₃ | Cl | 3-t-Bu |
| Cl | CF₃ | Cl | 4-OCHF₂ |
| Cl | CF₃ | CN | 4-Et |
| Cl | CF₃ | CN | 4-i-Pr |
| Cl | CF₃ | CN | 4-t-Bu |
| Cl | CF₃ | CN | 3-t-Bu |
| Cl | CF₃ | CN | 4-OCHF₂ |
| Cl | CF₃ | NHCHO | 4-Et |
| Cl | CF₃ | NHCHO | 4-i-Pr |
| Cl | CF₃ | NHCHO | 4-t-Bu |
| Cl | CF₃ | NHCHO | 3-t-Bu |
| Cl | CF₃ | NHCHO | 4-OCHF₂ |
| Cl | CF₃ | NHCOCH₃ | 4-Et |
| Cl | CF₃ | NHCOCH₃ | 4-i-Pr |
| Cl | CF₃ | NHCOCH₃ | 4-t-Bu |
| Cl | CF₃ | NHCOCH₃ | 3-t-Bu |
| Cl | CF₃ | NHCOCH₃ | 4-OCHF₂ |
| Cl | Et | H | 4-Et |
| Cl | Et | H | 4-i-Pr |
| Cl | Et | H | 4-t-Bu |
| Cl | Et | H | 3-t-Bu |
| Cl | Et | H | 4-OCHF₂ |
| Cl | Et | Cl | 4-Et |
| Cl | Et | Cl | 4-i-Pr |
| Cl | Et | Cl | 4-t-Bu |
| Cl | Et | Cl | 3-t-Bu |
| Cl | Et | Cl | 4-OCHF₂ |
| Cl | Et | Br | 4-Et |
| Cl | Et | Br | 4-i-Pr |
| Cl | Et | Br | 4-t-Bu |
| Cl | Et | Br | 3-t-Bu |
| Cl | Et | Br | 4-OCHF₂ |
| Cl | Et | I | 4-Et |
| Cl | Et | I | 4-i-Pr |
| Cl | Et | I | 4-t-Bu |
| Cl | Et | I | 3-t-Bu |
| Cl | Et | I | 4-OCHF₂ |
| Cl | Cl | H | 4-Et |
| Cl | Cl | H | 4-i-Pr |
| Cl | Cl | H | 4-t-Bu |
| Cl | Cl | H | 3-t-Bu |
| Cl | Cl | H | 4-OCHF₂ |
| Cl | Cl | Cl | 4-Et |
| Cl | Cl | Cl | 4-i-Pr |
| Cl | Cl | Cl | 4-t-Bu |
| Cl | Cl | Cl | 3-t-Bu |
| Cl | Cl | Cl | 4-OCHF₂ |
| CH₂Cl | Me | H | 4-Et |
| CH₂Cl | Me | H | 4-i-Pr |
| CH₂Cl | Me | H | 4-t-Bu |
| CH₂Cl | Me | H | 3-t-Bu |
| CH₂Cl | Me | H | 4-OCHF₂ |
| OMe | Me | H | 4-Et |
| OMe | Me | H | 4-i-Pr |
| OMe | Me | H | 4-t-Bu |
| OMe | Me | H | 3-t-Bu |
| OMe | Me | H | 4-OCHF₂ |
| OMe | Me | Cl | 4-Et |
| OMe | Me | Cl | 4-i-Pr |
| OMe | Me | Cl | 4-t-Bu |
| OMe | Me | Cl | 3-t-Bu |
| OMe | Me | Cl | 4-OCHF₂ |
| OCHF₂ | Me | H | 4-Et |

TABLE 1-continued

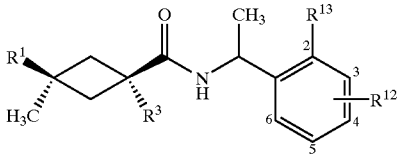

| R¹ | R³ | R¹³ | R¹² |
|---|---|---|---|
| OCHF$_2$ | Me | H | 4-i-Pr |
| OCHF$_2$ | Me | H | 4-t-Bu |
| OCHF$_2$ | Me | H | 3-t-Bu |
| OCHF$_2$ | Me | H | 4-OCHF$_2$ |
| OCHF$_2$ | Me | Cl | 4-Et |
| OCHF$_2$ | Me | Cl | 4-i-Pr |
| OCHF$_2$ | Me | Cl | 4-t-Bu |
| OCHF$_2$ | Me | Cl | 3-t-Bu |
| OCHF$_2$ | Me | Cl | 4-OCHF$_2$ |

TABLE 2

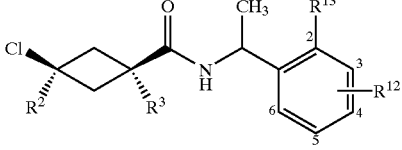

| R² | R³ | R¹³ | R¹² |
|---|---|---|---|
| Column 1 | | | |
| Cl | Cl | H | 4-Me |
| Cl | Cl | H | 4-Cl |
| Cl | Cl | H | 4-Br |
| Cl | Cl | H | 4-I |
| Cl | Cl | H | 4-CF$_3$ |
| Cl | Cl | Cl | 4-Me |
| Cl | Cl | Cl | 4-Cl |
| Cl | Cl | Cl | 4-Br |
| Cl | Cl | Cl | 4-I |
| Cl | Cl | Cl | 4-CF$_3$ |
| CH$_2$Cl | Me | H | 4-Me |
| CH$_2$Cl | Me | H | 4-Cl |
| CH$_2$Cl | Me | H | 4-Br |
| CH$_2$Cl | Me | H | 4-I |
| CH$_2$Cl | Me | H | 4-CF$_3$ |
| CH$_2$Cl | Me | Cl | 4-Me |
| CH$_2$Cl | Me | Cl | 4-Cl |
| CH$_2$Cl | Me | Cl | 4-Br |
| CH$_2$Cl | Me | Cl | 4-I |
| CH$_2$Cl | Me | Cl | 4-CF$_3$ |
| CH$_2$Cl | CH$_2$F | H | 4-Me |
| CH$_2$Cl | CH$_2$F | H | 4-Cl |
| CH$_2$Cl | CH$_2$F | H | 4-Br |
| CH$_2$Cl | CH$_2$F | H | 4-I |
| CH$_2$Cl | CH$_2$F | H | 4-CF$_3$ |
| CH$_2$Cl | CH$_2$F | Cl | 4-Me |
| CH$_2$Cl | CH$_2$F | Cl | 4-Cl |
| CH$_2$Cl | CH$_2$F | Cl | 4-Br |
| CH$_2$Cl | CH$_2$F | Cl | 4-I |
| CH$_2$Cl | CH$_2$F | Cl | 4-CF$_3$ |
| CH$_2$Cl | CHF$_2$ | H | 4-Me |
| CH$_2$Cl | CHF$_2$ | H | 4-Cl |
| CH$_2$Cl | CHF$_2$ | H | 4-Br |
| CH$_2$Cl | CHF$_2$ | H | 4-I |
| CH$_2$Cl | CHF$_2$ | H | 4-CF$_3$ |
| CH$_2$Cl | CHF$_2$ | Cl | 4-Me |
| CH$_2$Cl | CHF$_2$ | Cl | 4-Cl |
| CH$_2$Cl | CHF$_2$ | Cl | 4-Br |
| CH$_2$Cl | CHF$_2$ | Cl | 4-I |
| CH$_2$Cl | CHF$_2$ | Cl | 4-CF$_3$ |
| CH$_2$Cl | CF$_3$ | H | 4-Me |

TABLE 2-continued

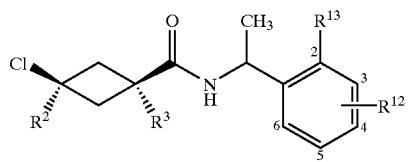

| R² | R³ | R¹³ | R¹² |
|---|---|---|---|
| CH$_2$Cl | CF$_3$ | H | 4-Cl |
| CH$_2$Cl | CF$_3$ | H | 4-Br |
| CH$_2$Cl | CF$_3$ | H | 4-I |
| CH$_2$Cl | CF$_3$ | H | 4-CF$_3$ |
| CH$_2$Cl | CF$_3$ | Cl | 4-Me |
| CH$_2$Cl | CF$_3$ | Cl | 4-Cl |
| CH$_2$Cl | CF$_3$ | Cl | 4-Br |
| CH$_2$Cl | CF$_3$ | Cl | 4-I |
| CH$_2$Cl | CF$_3$ | Cl | 4-CF$_3$ |
| Column 2 | | | |
| Cl | Cl | H | 4-Et |
| Cl | Cl | H | 4-i-Pr |
| Cl | Cl | H | 4-t-Bu |
| Cl | Cl | H | 3-t-Bu |
| Cl | Cl | H | 4-OCHF$_2$ |
| Cl | Cl | Cl | 4-Et |
| Cl | Cl | Cl | 4-i-Pr |
| Cl | Cl | Cl | 4-t-Bu |
| Cl | Cl | Cl | 3-t-Bu |
| Cl | Cl | Cl | 4-OCHF$_2$ |
| CH$_2$Cl | Me | H | 4-Et |
| CH$_2$Cl | Me | H | 4-i-Pr |
| CH$_2$Cl | Me | H | 4-t-Bu |
| CH$_2$Cl | Me | H | 3-t-Bu |
| CH$_2$Cl | Me | H | 4-OCHF$_2$ |
| CH$_2$Cl | Me | Cl | 4-Et |
| CH$_2$Cl | Me | Cl | 4-i-Pr |
| CH$_2$Cl | Me | Cl | 4-t-Bu |
| CH$_2$Cl | Me | Cl | 3-t-Bu |
| CH$_2$Cl | Me | Cl | 4-OCHF$_2$ |
| CH$_2$Cl | CH$_2$F | H | 4-Et |
| CH$_2$Cl | CH$_2$F | H | 4-i-Pr |
| CH$_2$Cl | CH$_2$F | H | 4-t-Bu |
| CH$_2$Cl | CH$_2$F | H | 3-t-Bu |
| CH$_2$Cl | CH$_2$F | H | 4-OCHF$_2$ |
| CH$_2$Cl | CH$_2$F | Cl | 4-Et |
| CH$_2$Cl | CH$_2$F | Cl | 4-i-Pr |
| CH$_2$Cl | CH$_2$F | Cl | 4-t-Bu |
| CH$_2$Cl | CH$_2$F | Cl | 3-t-Bu |
| CH$_2$Cl | CH$_2$F | Cl | 4-OCHF$_2$ |
| CH$_2$Cl | CHF$_2$ | H | 4-Et |
| CH$_2$Cl | CHF$_2$ | H | 4-i-Pr |
| CH$_2$Cl | CHF$_2$ | H | 4-t-Bu |
| CH$_2$Cl | CHF$_2$ | H | 3-t-Bu |
| CH$_2$Cl | CHF$_2$ | H | 4-OCHF$_2$ |
| CH$_2$Cl | CHF$_2$ | Cl | 4-Et |
| CH$_2$Cl | CHF$_2$ | Cl | 4-i-Pr |
| CH$_2$Cl | CHF$_2$ | Cl | 4-t-Bu |
| CH$_2$Cl | CHF$_2$ | Cl | 3-t-Bu |
| CH$_2$Cl | CHF$_2$ | Cl | 4-OCHF$_2$ |
| CH$_2$Cl | CF$_3$ | H | 4-Et |
| CH$_2$Cl | CF$_3$ | H | 4-i-Pr |

TABLE 2-continued

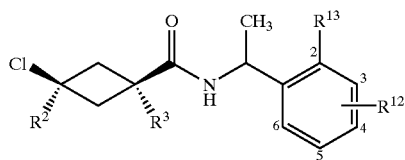

| R² | R³ | R¹³ | R¹² |
|---|---|---|---|
| CH₂Cl | CF₃ | H | 4-t-Bu |
| CH₂Cl | CF₃ | H | 3-t-Bu |
| CH₂Cl | CF₃ | H | 4-OCHF₂ |
| CH₂Cl | CF₃ | Cl | 4-Et |
| CH₂Cl | CF₃ | Cl | 4-i-Pr |
| CH₂Cl | CF₃ | Cl | 4-t-Bu |
| CH₂Cl | CF₃ | Cl | 3-t-Bu |
| CH₂Cl | CF₃ | Cl | 4-OCHF₂ |

TABLE 3

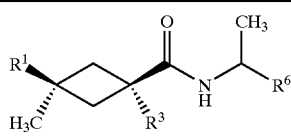

| R¹ | R³ | R⁶ |
|---|---|---|
| *Column 1* | | |
| H | Me | 1-naphthylenyl |
| H | Me | 5-Cl-2-thienyl |
| H | Me | 3,5-diCl-2-thienyl |
| H | Me | 2-Cl-5-thiazoyl |
| H | Me | 3-Me-5-isothiazoyl |
| Cl | Me | 1-naphthylenyl |
| Cl | Me | 5-Cl-2-thienyl |
| Cl | Me | 3,5-diCl-2-thienyl |
| Cl | Me | 2-Cl-5-thiazoyl |
| Cl | Me | 3-Me-5-isothiazoyl |
| Cl | CH₂F | 1-naphthylenyl |
| Cl | CH₂F | 5-Cl-2-thienyl |
| Cl | CH₂F | 3,5-diCl-2-thienyl |
| Cl | CH₂F | 2-Cl-5-thiazoyl |
| Cl | CH₂F | 3-Me-5-isothiazoyl |
| Cl | CHF₂ | 1-naphthylenyl |
| Cl | CHF₂ | 5-Cl-2-thienyl |
| Cl | CHF₂ | 3,5-diCl-2-thienyl |
| Cl | CHF₂ | 2-Cl-5-thiazoyl |
| Cl | CHF₂ | 3-Me-5-isothiazoyl |
| Cl | CF₃ | 1-naphthylenyl |
| Cl | CF₃ | 5-Cl-2-thienyl |
| Cl | CF₃ | 3,5-diCl-2-thienyl |
| Cl | CF₃ | 2-Cl-5-thiazoyl |
| Cl | CF₃ | 3-Me-5-isothiazoyl |
| Cl | Cl | 1-naphthylenyl |
| Cl | Cl | 5-Cl-2-thienyl |
| Cl | Cl | 3,5-diCl-2-thienyl |
| Cl | Cl | 2-Cl-5-thiazoyl |
| Cl | Cl | 3-Me-5-isothiazoyl |
| CH₂Cl | Me | 1-naphthylenyl |
| CH₂Cl | Me | 5-Cl-2-thienyl |
| CH₂Cl | Me | 3,5-diCl-2-thienyl |
| CH₂Cl | Me | 2-Cl-5-thiazoyl |
| CH₂Cl | Me | 3-Me-5-isothiazoyl |
| *Column 2* | | |
| H | Me | 2-naphthylenyl |
| H | Me | 5-Br-2-thienyl |
| H | Me | 5-Me-2-thiazoyl |
| H | Me | 2,4-diCl-5-thiazoyl |
| H | Me | 2-benzthiazolyl |
| Cl | Me | 2-naphthylenyl |
| Cl | Me | 5-Br-2-thienyl |
| Cl | Me | 5-Me-2-thiazoyl |
| Cl | Me | 2,4-diCl-5-thiazoyl |
| Cl | Me | 2-benzthiazolyl |
| Cl | CH₂F | 2-naphthylenyl |
| Cl | CH₂F | 5-Br-2-thienyl |
| Cl | CH₂F | 5-Me-2-thiazoyl |
| Cl | CH₂F | 2,4-diCl-5-thiazoyl |
| Cl | CH₂F | 2-benzthiazolyl |
| Cl | CHF₂ | 2-naphthylenyl |
| Cl | CHF₂ | 5-Br-2-thienyl |
| Cl | CHF₂ | 5-Me-2-thiazoyl |
| Cl | CHF₂ | 2,4-diCl-5-thiazoyl |
| Cl | CHF₂ | 2-benzthiazolyl |
| Cl | CF₃ | 2-naphthylenyl |
| Cl | CF₃ | 5-Br-2-thienyl |
| Cl | CF₃ | 5-Me-2-thiazoyl |
| Cl | CF₃ | 2,4-diCl-5-thiazoyl |
| Cl | CF₃ | 2-benzthiazolyl |
| Cl | Cl | 2-naphthylenyl |
| Cl | Cl | 5-Br-2-thienyl |
| Cl | Cl | 5-Me-2-thiazoyl |
| Cl | Cl | 2,4-diCl-5-thiazoyl |
| Cl | Cl | 2-benzthiazolyl |
| CH₂Cl | Me | 2-naphthylenyl |
| CH₂Cl | Me | 5-Br-2-thienyl |
| CH₂Cl | Me | 5-Me-2-thiazoyl |
| CH₂Cl | Me | 2,4-diCl-5-thiazoyl |
| CH₂Cl | Me | 2-benzthiazolyl |

TABLE 4

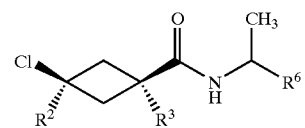

| R² | R³ | R⁶ |
|---|---|---|
| *Column 1* | | |
| Cl | Cl | 1-naphthylenyl |
| Cl | Cl | 5-Cl-2-thienyl |
| Cl | Cl | 3.5-diCl-2-thienyl |
| Cl | Cl | 2-Cl-5-thiazoyl |
| Cl | Cl | 3-Me-5-isothiazoyl |
| CH₂Cl | Me | 1-naphthylenyl |
| CH₂Cl | Me | 5-Cl-2-thienyl |
| CH₂Cl | Me | 3,5-diCl-2-thienyl |
| CH₂Cl | Me | 2-Cl-5-thiazoyl |
| CH₂Cl | Me | 3-Me-5-isothiazoyl |
| CH₂Cl | CF₃ | 1-naphthylenyl |
| CH₂Cl | CF₃ | 5-Cl-2-thienyl |
| CH₂Cl | CF₃ | 3,5-diCl-2-thienyl |
| CH₂Cl | CF₃ | 2-Cl-5-thiazoyl |
| CH₂Cl | CF₃ | 3-Me-5-isothiazoyl |
| *Column 2* | | |
| Cl | Cl | 2-naphthylenyl |
| Cl | Cl | 5-Br-2-thienyl |
| Cl | Cl | 5-Me-2-thiazoyl |
| Cl | Cl | 2.4-diCl-5-thiazoyl |
| Cl | Cl | 2-benzthiazolyl |
| CH₂Cl | Me | 2-naphthylenyl |
| CH₂Cl | Me | 5-Br-2-thienyl |
| CH₂Cl | Me | 5-Me-2-thiazoyl |
| CH₂Cl | Me | 2,4-diCl-5-thiazoyl |

TABLE 4-continued

Structure: cyclobutane with Cl and R² on one carbon, R³ and C(=O)NH-CH(CH₃)-R⁶ on the other.

| R² | R³ | R⁶ |
|---|---|---|
| CH$_2$Cl | Me | 2-benzthiazolyl |
| CH$_2$Cl | CF$_3$ | 2-naphthylenyl |
| CH$_2$Cl | CF$_3$ | 5-Br-2-thienyl |
| CH$_2$Cl | CF$_3$ | 5-Me-2-thiazoyl |
| CH$_2$Cl | CF$_3$ | 2,4-diCl-5-thiazoyl |
| CH$_2$Cl | CF$_3$ | 2-benzthiazolyl |

TABLE 5

Structure: cyclobutane with R¹ and CH₃ on one carbon, R³ and C(=O)NH-CH(CH₃)-CH₂-O-R⁶ on the other.

| R¹ | R³ | R⁶ |
|---|---|---|

Column 1

| R¹ | R³ | R⁶ |
|---|---|---|
| Cl | Me | 2-F—C$_6$H$_4$ |
| Cl | Me | 2-F-5-Me—C$_6$H$_3$ |
| Cl | Me | 2,5-diF—C$_6$H$_3$ |
| Cl | Me | 2-F-5-Cl—C$_6$H$_3$ |
| Cl | Me | 2-Cl-5-F—C$_6$H$_3$ |
| Cl | Me | 2,5-diCl—C$_6$H$_3$ |
| Cl | Me | 2-CN-5-Me—C$_6$H$_3$ |
| Cl | Me | 2-CN-5-F—C$_6$H$_3$ |
| Cl | Me | 2-CN-5-Cl—C$_6$H$_3$ |
| Cl | CH$_2$F | 2-F—C$_6$H$_4$ |
| Cl | CH$_2$F | 2-F-5-Me—C$_6$H$_3$ |
| Cl | CH$_2$F | 2,5-diF—C$_6$H$_3$ |
| Cl | CH$_2$F | 2-F-5-Cl—C$_6$H$_3$ |
| Cl | CH$_2$F | 2-Cl-5-F—C$_6$H$_3$ |
| Cl | CH$_2$F | 2,5-diCl—C$_6$H$_3$ |
| Cl | CH$_2$F | 2-CN-5-F—C$_6$H$_3$ |
| Cl | CH$_2$F | 2-CN-5-Me—C$_6$H$_3$ |
| Cl | CH$_2$F | 2-CN-5-Cl—C$_6$H$_3$ |
| Cl | CHF$_2$ | 2-F—C$_6$H$_4$ |
| Cl | CHF$_2$ | 2-F-5-Me—C$_6$H$_3$ |
| Cl | CHF$_2$ | 2,5-diF—C$_6$H$_3$ |
| Cl | CHF$_2$ | 2-F-5-Cl—C$_6$H$_3$ |
| Cl | CHF$_2$ | 2-Cl-5-F—C$_6$H$_3$ |
| Cl | CHF$_2$ | 2,5-diCl—C$_6$H$_3$ |
| Cl | CHF$_2$ | 2-CN-5-F—C$_6$H$_3$ |
| Cl | CHF$_2$ | 2-CN-5-Me—C$_6$H$_3$ |
| Cl | CHF$_2$ | 2-CN-5-Cl—C$_6$H$_3$ |
| Cl | CF$_3$ | 2-F—C$_6$H$_4$ |
| Cl | CF$_3$ | 2-F-5-Me—C$_6$H$_3$ |
| Cl | CF$_3$ | 2,5-diF—C$_6$H$_3$ |
| Cl | CF$_3$ | 2-F-5-Cl—C$_6$H$_3$ |
| Cl | CF$_3$ | 2-Cl-5-F—C$_6$H$_3$ |
| Cl | CF$_3$ | 2,5-diCl—C$_6$H$_3$ |
| Cl | CF$_3$ | 2-CN-5-F—C$_6$H$_3$ |
| Cl | CF$_3$ | 2-CN-5-Me—C$_6$H$_3$ |
| Cl | CF$_3$ | 2-CN-5-Cl—C$_6$H$_3$ |
| Cl | Cl | 2-F—C$_6$H$_4$ |
| Cl | Cl | 2-F-5-Me—C$_6$H$_3$ |
| Cl | Cl | 2,5-diF—C$_6$H$_3$ |
| Cl | Cl | 2-F-5-Cl—C$_6$H$_3$ |
| Cl | Cl | 2-Cl-5-F—C$_6$H$_3$ |
| Cl | Cl | 2,5-diCl—C$_6$H$_3$ |
| Cl | Cl | 2-CN-5-F—C$_6$H$_3$ |
| Cl | Cl | 2-CN-5-Me—C$_6$H$_3$ |
| Cl | Cl | 2-CN-5-Cl—C$_6$H$_3$ |

TABLE 5-continued

Column 2

| R¹ | R³ | R⁶ |
|---|---|---|
| Cl | Me | 2-CN-5-OMe—C$_6$H$_3$ |
| Cl | Me | 2-CN-5-OCHF$_2$—C$_6$H$_3$ |
| Cl | Me | 3-Cl-2-thienyl |
| Cl | Me | 4-Cl-5-thiazoyl |
| Cl | Me | 4-Cl-5-isothiazoyl |
| Cl | Me | 2-Cl-1H-pyrrol-1-yl |
| Cl | Me | 2,4-diCl-1H-pyrrol-1-yl |
| Cl | Me | 2-CN-5-Br—C$_6$H$_3$ |
| Cl | Me | 2-benzthiazoyl |
| Cl | CH$_2$F | 2-CN-5-OMe—C$_6$H$_3$ |
| Cl | CH$_2$F | 2-CN-5-OCHF$_2$—C$_6$H$_3$ |
| Cl | CH$_2$F | 3-Cl-2-thienyl |
| Cl | CH$_2$F | 4-Cl-5-thiazoyl |
| Cl | CH$_2$F | 4-Cl-5-isothiazoyl |
| Cl | CH$_2$F | 2-Cl-1H-pyrrol-1-yl |
| Cl | CH$_2$F | 2-CN-5-Br—C$_6$H$_3$ |
| Cl | CH$_2$F | 2,4-diCl-1H-pyrrol-1-yl |
| Cl | CH$_2$F | 2-benzthiazoyl |
| Cl | CHF$_2$ | 2-CN-5-OMe—C$_6$H$_3$ |
| Cl | CHF$_2$ | 2-CN-5-OCHF$_2$—C$_6$H$_3$ |
| Cl | CHF$_2$ | 3-Cl-2-thienyl |
| Cl | CHF$_2$ | 4-Cl-5-thiazoyl |
| Cl | CHF$_2$ | 4-Cl-5-isothiazoyl |
| Cl | CHF$_2$ | 2-Cl-1H-pyrrol-1-yl |
| Cl | CHF$_2$ | 2-CN-5-Br—C$_6$H$_3$ |
| Cl | CHF$_2$ | 2,4-diCl-1H-pyrrol-1-yl |
| Cl | CHF$_2$ | 2-benzthiazoyl |
| Cl | CF$_3$ | 2-CN-5-OMe—C$_6$H$_3$ |
| Cl | CF$_3$ | 2-CN-5-OCHF$_2$—C$_6$H$_3$ |
| Cl | CF$_3$ | 3-Cl-2-thienyl |
| Cl | CF$_3$ | 4-Cl-5-thiazoyl |
| Cl | CF$_3$ | 4-Cl-5-isothiazoyl |
| Cl | CF$_3$ | 2-Cl-1H-pyrrol-1-yl |
| Cl | CF$_3$ | 2-CN-5-Br—C$_6$H$_3$ |
| Cl | CF$_3$ | 2,4-diCl-1H-pyrrol-1-yl |
| Cl | CF$_3$ | 2-benzthiazoyl |
| Cl | Cl | 2-CN-5-OMe—C$_6$H$_3$ |
| Cl | Cl | 2-CN-5-OCHF$_2$—C$_6$H$_3$ |
| Cl | Cl | 3-Cl-2-thienyl |
| Cl | Cl | 4-Cl-5-thiazoyl |
| Cl | Cl | 4-Cl-5-isothiazoyl |
| Cl | Cl | 2-Cl-1H-pyrrol-1-yl |
| Cl | Cl | 2-CN-5-Br—C$_6$H$_3$ |
| Cl | Cl | 2,4-diCl-1H-pyrrol-1-yl |
| Cl | Cl | 2-benzthiazoyl |

TABLE 6

Structure: cyclobutane with Cl and R² on one carbon, R³ and C(=O)NH-CH(CH₃)-CH₂-O-R⁶ on the other.

| R² | R³ | R⁶ |
|---|---|---|

Column 1

| R² | R³ | R⁶ |
|---|---|---|
| Cl | Cl | 2-F—C$_6$H$_4$ |
| Cl | Cl | 2-F-5-Me—C$_6$H$_3$ |
| Cl | Cl | 2,5-diF—C$_6$H$_3$ |
| Cl | Cl | 2-F-5-Cl—C$_6$H$_3$ |
| Cl | Cl | 2-Cl-5-F—C$_6$H$_3$ |
| Cl | Cl | 2,5-diCl—C$_6$H$_3$ |
| Cl | Cl | 2-CN-5-F—C$_6$H$_3$ |
| Cl | Cl | 2-CN-5-Me—C$_6$H$_3$ |

TABLE 6-continued

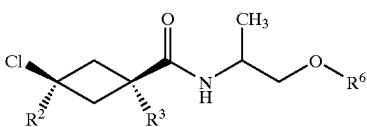

| $R^2$ | $R^3$ | $R^6$ |
|---|---|---|
| Cl | Cl | 2-CN-5-Cl—$C_6H_3$ |
| $CH_2Cl$ | Me | 2-F—$C_6H_4$ |
| $CH_2Cl$ | Me | 2-F-5-Me—$C_6H_3$ |
| $CH_2Cl$ | Me | 2,5-diF—$C_6H_3$ |
| $CH_2Cl$ | Me | 2-F-5-Cl—$C_6H_3$ |
| $CH_2Cl$ | Me | 2-Cl-5-F—$C_6H_3$ |
| $CH_2Cl$ | Me | 2,5-diCl—$C_6H_3$ |
| $CH_2Cl$ | Me | 2-CN-5-F—$C_6H_3$ |
| $CH_2Cl$ | Me | 2-CN-5-Me—$C_6H_3$ |
| $CH_2Cl$ | Me | 2-CN-5-Cl—$C_6H_3$ |
| $CH_2Cl$ | $CF_3$ | 2-F—$C_6H_4$ |
| $CH_2Cl$ | $CF_3$ | 2-F-5-Me—$C_6H_3$ |
| $CH_2Cl$ | $CF_3$ | 2,5-diF—$C_6H_3$ |
| $CH_2Cl$ | $CF_3$ | 2-F-5-Cl—$C_6H_3$ |
| $CH_2Cl$ | $CF_3$ | 2-Cl-5-F—$C_6H_3$ |
| $CH_2Cl$ | $CF_3$ | 2,5-diCl—$C_6H_3$ |
| $CH_2Cl$ | $CF_3$ | 2-CN-5-F—$C_6H_3$ |
| $CH_2Cl$ | $CF_3$ | 2-CN-5-Me—$C_6H_3$ |
| $CH_2Cl$ | $CF_3$ | 2-CN-5-Cl—$C_6H_3$ |

Column 2

| $R^2$ | $R^3$ | $R^6$ |
|---|---|---|
| Cl | Cl | 2-CN-5-OMe—$C_6H_3$ |
| Cl | Cl | 2-CN-5-OCHF$_2$—$C_6H_3$ |
| Cl | Cl | 3-Cl-2-thienyl |
| Cl | Cl | 4-Cl-5-thiazoyl |
| Cl | Cl | 4-Cl-5-isothiazoyl |
| Cl | Cl | 2-Cl-1H-pyrrol-yl |
| Cl | Cl | 2-CN-5-Br—$C_6H_3$ |
| Cl | Cl | 2,4-diCl-1H-pyrrol-1-yl |
| Cl | Cl | 2-benzthiazoyl |
| $CH_2Cl$ | Me | 2-CN-5-OMe—$C_6H_3$ |
| $CH_2Cl$ | Me | 2-CN-5-OCHF$_2$—$C_6H_3$ |
| $CH_2Cl$ | Me | 3-Cl-2-thienyl |
| $CH_2Cl$ | Me | 4-Cl-5-thiazoyl |
| $CH_2Cl$ | Me | 4-Cl-5-isothiazoyl |
| $CH_2Cl$ | Me | 2-Cl-1H-pyrrol-1-yl |
| $CH_2Cl$ | Me | 2-CN-5-Br—$C_6H_3$ |
| $CH_2Cl$ | Me | 2,4-diCl-1H-pyrrol-1-yl |
| $CH_2Cl$ | Me | 2-benzthiazoyl |
| $CH_2Cl$ | $CF_3$ | 2-CN-5-OMe—$C_6H_3$ |
| $CH_2Cl$ | $CF_3$ | 2-CN-5-OCHF$_2$—$C_6H_3$ |
| $CH_2Cl$ | $CF_3$ | 3-Cl-2-thienyl |
| $CH_2Cl$ | $CF_3$ | 4-Cl-5-thiazoyl |
| $CH_2Cl$ | $CF_3$ | 4-Cl-5-isothiazoyl |
| $CH_2Cl$ | $CF_3$ | 2-Cl-1H-pyrrol-1-yl |
| $CH_2Cl$ | $CF_3$ | 2-CN-5-Br—$C_6H_3$ |
| $CH_2Cl$ | $CF_3$ | 2,4-diCl-1H-pyrrol-1-yl |
| $CH_2Cl$ | $CF_3$ | 2-benzthiazoyl |

TABLE 7

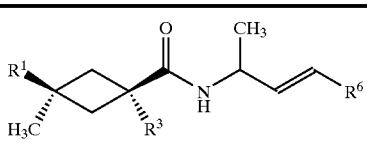

| $R^1$ | $R^3$ | $R^6$ |
|---|---|---|

Column 1

| $R^1$ | $R^3$ | $R^6$ |
|---|---|---|
| Cl | Me | 2-F—$C_6H_4$ |
| Cl | Me | 2-F-5-Me—$C_6H_3$ |
| Cl | Me | 2,5-diF—$C_6H_3$ |
| Cl | Me | 2-F-5-Cl—$C_6H_3$ |
| Cl | Me | 2-Cl-5-F—$C_6H_3$ |

TABLE 7-continued

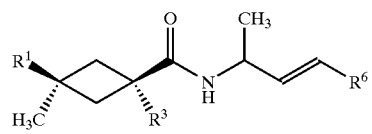

| $R^1$ | $R^3$ | $R^6$ |
|---|---|---|
| Cl | Me | 2,5-diCl—$C_6H_3$ |
| Cl | Me | 2-CN-5-F—$C_6H_3$ |
| Cl | Me | 2-CN-5-Me—$C_6H_3$ |
| Cl | $CH_2F$ | 2-F—$C_6H_4$ |
| Cl | $CH_2F$ | 2-F-5-Me—$C_6H_3$ |
| Cl | $CH_2F$ | 2,5-diF—$C_6H_3$ |
| Cl | $CH_2F$ | 2-F-5-Cl—$C_6H_3$ |
| Cl | $CH_2F$ | 2-Cl-5-F—$C_6H_3$ |
| Cl | $CH_2F$ | 2,5-diCl—$C_6H_3$ |
| Cl | $CH_2F$ | 2-CN-5-F—$C_6H_3$ |
| Cl | $CH_2F$ | 2-CN-5-Cl—$C_6H_3$ |
| Cl | $CHF_2$ | 2-F—$C_6H_4$ |
| Cl | $CHF_2$ | 2-F-5-Me—$C_6H_3$ |
| Cl | $CHF_2$ | 2,5-diF—$C_6H_3$ |
| Cl | $CHF_2$ | 2-F-5-Cl—$C_6H_3$ |
| Cl | $CHF_2$ | 2-Cl-5-F—$C_6H_3$ |
| Cl | $CHF_2$ | 2,5-diCl—$C_6H_3$ |
| Cl | $CHF_2$ | 2-CN-5-Me—$C_6H_3$ |
| Cl | $CF_3$ | 2-F—$C_6H_4$ |
| Cl | $CF_3$ | 2-F-5-Me—$C_6H_3$ |
| Cl | $CF_3$ | 2,5-diF—$C_6H_3$ |
| Cl | $CF_3$ | 2-CN-5-F—$C_6H_3$ |
| Cl | $CF_3$ | 2-F-5-Cl—$C_6H_3$ |
| Cl | $CF_3$ | 2-Cl-5-F—$C_6H_3$ |
| Cl | $CF_3$ | 2,5-diCl—$C_6H_3$ |
| Cl | $CF_3$ | 2-CN-5-Me—$C_6H_3$ |
| Cl | Cl | 2-F—$C_6H_4$ |
| Cl | Cl | 2-F-5-Me—$C_6H_3$ |
| Cl | Cl | 2,5-diF—$C_6H_3$ |
| Cl | Cl | 2-F-5-Cl—$C_6H_3$ |
| Cl | Cl | 2-Cl-5-F—$C_6H_3$ |
| Cl | Cl | 2,5-diCl—$C_6H_3$ |
| Cl | Cl | 2-CN-5-F—$C_6H_3$ |
| Cl | Cl | 2-CN-5-Me—$C_6H_3$ |

Column 2

| $R^1$ | $R^3$ | $R^6$ |
|---|---|---|
| Cl | Me | 2-CN-5-Cl—$C_6H_3$ |
| Cl | Me | 2-CN-5-OMe—$C_6H_3$ |
| Cl | Me | 2-CN-5-OCHF$_2$—$C_6H_3$ |
| Cl | Me | 3-Cl-2-thienyl |
| Cl | Me | 4-Cl-5-thiazoyl |
| Cl | Me | 4-Cl-5-isothiazoyl |
| Cl | Me | 2-CN-5-Br—$C_6H_3$ |
| Cl | Me | 2-benzthiazoyl |
| Cl | $CH_2F$ | 2-CN-5-Me—$C_6H_3$ |
| Cl | $CH_2F$ | 2-CN-5-OMe—$C_6H_3$ |
| Cl | $CH_2F$ | 2-CN-5-OCHF$_2$—$C_6H_3$ |
| Cl | $CH_2F$ | 3-Cl-2-thienyl |
| Cl | $CH_2F$ | 4-Cl-5-thiazoyl |
| Cl | $CH_2F$ | 4-Cl-5-isothiazoyl |
| Cl | $CH_2F$ | 2-CN-5-Br—$C_6H_3$ |
| Cl | $CH_2F$ | 2-benzthiazoyl |
| Cl | $CHF_2$ | 2-CN-5-Cl—$C_6H_3$ |
| Cl | $CHF_2$ | 2-CN-5-OMe—$C_6H_3$ |
| Cl | $CHF_2$ | 2-CN-5-OCHF$_2$—$C_6H_3$ |
| Cl | $CHF_2$ | 3-Cl-2-thienyl |
| Cl | $CHF_2$ | 4-Cl-5-thiazoyl |
| Cl | $CHF_2$ | 4-Cl-5-isothiazoyl |
| Cl | $CHF_2$ | 2-benzthiazoyl |
| Cl | $CF_3$ | 2-CN-5-Cl—$C_6H_3$ |
| Cl | $CF_3$ | 2-CN-5-OMe—$C_6H_3$ |
| Cl | $CF_3$ | 2-CN-5-OCHF$_2$—$C_6H_3$ |
| Cl | $CF_3$ | 2-CN-5-Br—$C_6H_3$ |
| Cl | $CF_3$ | 3-Cl-2-thienyl |
| Cl | $CF_3$ | 4-Cl-5-thiazoyl |
| Cl | $CF_3$ | 4-Cl-5-isothiazoyl |
| Cl | $CF_3$ | 2-benzthiazoyl |
| Cl | Cl | 2-CN-5-Cl—$C_6H_3$ |
| Cl | Cl | 2-CN-5-OMe—$C_6H_3$ |

TABLE 7-continued

Structure: R¹ and H₃C on one carbon of cyclobutane; R³ on the other carbon bearing C(=O)NH-CH(CH₃)-CH=CH-R⁶

| R¹ | R³ | R⁶ |
|---|---|---|
| Cl | Cl | 2-CN-5-OCHF$_2$—C$_6$H$_3$ |
| Cl | Cl | 3-Cl-2-thienyl |
| Cl | Cl | 4-Cl-5-thiazoyl |
| Cl | Cl | 4-Cl-5-isothiazoyl |
| Cl | Cl | 2-CN-5-Br—C$_6$H$_3$ |
| Cl | Cl | 2-benzthiazoyl |

TABLE 8

Structure: Cl and R² on one carbon of cyclobutane; R³ on the other carbon bearing C(=O)NH-CH(CH₃)-CH=CH-R⁶

| R² | R³ | R⁶ |
|---|---|---|
| *Column 1* | | |
| Cl | Cl | 2-F—C$_6$H$_4$ |
| Cl | Cl | 2-F-5-Me—C$_6$H$_3$ |
| Cl | Cl | 2,5-diF—C$_6$H$_3$ |
| Cl | Cl | 2-F-5-Cl—C$_6$H$_3$ |
| Cl | Cl | 2-Cl-5-F—C$_6$H$_3$ |
| Cl | Cl | 2,5-diCl—C$_6$H$_3$ |
| Cl | Cl | 2-CN-5-Me—C$_6$H$_3$ |
| CH$_2$Cl | Me | 2-F—C$_6$H$_4$ |
| CH$_2$Cl | Me | 2-F-5-Me—C$_6$H$_3$ |
| CH$_2$Cl | Me | 2,5-diF—C$_6$H$_3$ |
| CH$_2$Cl | Me | 2-F-5-Cl—C$_6$H$_3$ |
| CH$_2$Cl | Me | 2-Cl-5-F—C$_6$H$_3$ |
| CH$_2$Cl | Me | 2,5-diCl—C$_6$H$_3$ |
| CH$_2$Cl | Me | 2-CN-5-F—C$_6$H$_3$ |
| CH$_2$Cl | Me | 2-CN-5-Me—C$_6$H$_3$ |
| CH$_2$Cl | CF$_3$ | 2-F—C$_6$H$_4$ |
| CH$_2$Cl | CF$_3$ | 2-F-5-Me—C$_6$H$_3$ |
| CH$_2$Cl | CF$_3$ | 2,5-diF—C$_6$H$_3$ |
| CH$_2$Cl | CF$_3$ | 2-F-5-Cl—C$_6$H$_3$ |
| CH$_2$Cl | CF$_3$ | 2-Cl-5-F—C$_6$H$_3$ |
| CH$_2$Cl | CF$_3$ | 2,5-diCl—C$_6$H$_3$ |
| CH$_2$Cl | CF$_3$ | 2-CN-5-F—C$_6$H$_3$ |
| CH$_2$Cl | CF$_3$ | 2-CN-5-Me—C$_6$H$_3$ |
| *Column 2* | | |
| Cl | Cl | 2-CN-5-Cl—C$_6$H$_3$ |
| Cl | Cl | 2-CN-5-OMe—C$_6$H$_3$ |
| Cl | Cl | 2-CN-5-OCHF$_2$—C$_6$H$_3$ |
| Cl | Cl | 3-Cl-2-thienyl |
| Cl | Cl | 4-Cl-5-thiazoyl |
| Cl | Cl | 4-Cl-5-isothiazoyl |
| Cl | Cl | 2-benzthiazoyl |
| CH$_2$Cl | Me | 2-CN-5-Cl—C$_6$H$_3$ |
| CH$_2$Cl | Me | 2-CN-5-OMe—C$_6$H$_3$ |
| CH$_2$Cl | Me | 2-CN-5-OCHF$_2$—C$_6$H$_3$ |
| CH$_2$Cl | Me | 3-Cl-2-thienyl |
| CH$_2$Cl | Me | 4-Cl-5-thiazoyl |
| CH$_2$Cl | Me | 4-Cl-5-isothiazoyl |
| CH$_2$Cl | Me | 2-CN-5-Br—C$_6$H$_3$ |
| CH$_2$Cl | Me | 2-benzthiazoyl |
| CH$_2$Cl | CF$_3$ | 2-CN-5-Cl—C$_6$H$_3$ |
| CH$_2$Cl | CF$_3$ | 2-CN-5-OMe—C$_6$H$_3$ |
| CH$_2$Cl | CF$_3$ | 2-CN-5-OCHF$_2$—C$_6$H$_3$ |
| CH$_2$Cl | CF$_3$ | 3-Cl-2-thienyl |
| CH$_2$Cl | CF$_3$ | 4-Cl-5-thiazoyl |
| CH$_2$Cl | CF$_3$ | 4-Cl-5-isothiazoyl |

TABLE 8-continued

| R² | R³ | R⁶ |
|---|---|---|
| CH$_2$Cl | CF$_3$ | 2-CN-5-Br—C$_6$H$_3$ |
| CH$_2$Cl | CF$_3$ | 2-benzthiazoyl |

TABLE 9

Structure: R¹ and H₃C on one carbon of cyclobutane; R³ on the other carbon bearing C(=O)NH-CH(CH₃)-CH(R⁸)-O-R⁶

| R¹ | R³ | R⁶ | R⁸ |
|---|---|---|---|
| *Column 1* | | | |
| Cl | H | 2-CN-5-F—C$_6$H$_3$ | Me |
| Cl | Me | 2-CN-5-F—C$_6$H$_3$ | Me |
| Cl | H | 2,5-diF—C$_6$H$_3$ | Me |
| Cl | Me | 2,5-diF—C$_6$H$_3$ | Me |
| Br | H | 2-CN-5-F—C$_6$H$_3$ | Me |
| Br | Me | 2-CN-5-F—C$_6$H$_3$ | Me |
| Br | H | 2,5-diF—C$_6$H$_3$ | Me |
| Br | Me | 2,5-diF—C$_6$H$_3$ | Me |
| Cl | H | 2-CN-5-F—C$_6$H$_3$ | Et |
| Cl | H | 2,5-diF—C$_6$H$_3$ | Et |
| Br | H | 2-CN-5-F—C$_6$H$_3$ | Et |
| Br | H | 2,5-diF—C$_6$H$_4$ | Et |
| Cl | H | 2-CN-5-F—C$_6$H$_3$ | n-Bu |
| Cl | H | 2-CN-C$_6$H$_4$ | n-Bu |
| *Column 2* | | | |
| Cl | H | 2,5-diF—C$_6$H$_3$ | Ph |
| Cl | H | 2-CN—C$_6$H$_4$ | Ph |
| Cl | H | 2-CN-5-F—C$_6$H$_3$ | Ph |
| Br | H | 2-CN-5-F—C$_6$H$_3$ | Ph |
| Br | H | 2-CN—C$_6$H$_4$ | Ph |
| Cl | H | 2-CN-5-Cl—C$_6$H$_3$ | Ph |
| Cl | H | 2,5-diCl—C$_6$H$_3$ | 4-pyr |
| Br | H | 2,5-diF—C$_6$H$_3$ | 4-pyr |
| Cl | H | 2-CN-5-F—C$_6$H$_3$ | 4-MeO—Ph |
| Cl | H | 2-CN-5-F—C$_6$H$_3$ | 2-F—Ph |
| Cl | H | 2-CN-5-F—C$_6$H$_3$ | 3-F—Ph |
| Cl | H | 2-CN-5-F—C$_6$H$_3$ | 4-F—Ph |
| Cl | H | 2,5-diCl—C$_6$H$_3$ | 3-pyr |
| Cl | H | 2,5-diCl—C$_6$H$_3$ | 2-pyr |

FORMULATION/UTILITY

Compounds of this invention will generally be used as a formulation or composition with an agriculturally suitable carrier comprising at least one other component selected from the group consisting of surfactants, solid diluents and liquid diluents. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers,* 2nd Ed., Dorland Books, Caldwell, N.J. Typical liquid diluents are described in Marsden, *Solvents Guide,* 2nd Ed., Interscience, New York, 1950. *McCutcheon's Detergents and Emulsifiers Annual,* Allured Publ. Corp., Ridgewood, N.J., as well as Sisely and Wood, *Encyclopedia of Surface Active Agents,* Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering,* Dec. 4, 1967, pp 147–48, *Perry's Chemical Engineer's Handbook,* 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science,* John Wiley and Sons, Inc., New York, 1961, pp 81–96; and Hance et al., *Weed Control Handbook,* 8th Ed., Blackwell Scientific Publications, Oxford, 1989.

In the following Examples, all percentages are by weight and all formulations are prepared in conventional ways. Compound numbers refer to compounds in Index Tables A–D.

EXAMPLE A

| Wettable Powder | |
| --- | --- |
| Compound 30 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

EXAMPLE B

| Granule | |
| --- | --- |
| Compound 30 | 10.0% |
| attapulgite granules (low volatile matter, 0.71/0.30 mm; U.S.S. No. 25–50 sieves) | 90.0%. |

EXAMPLE C

| Extruded Pellet | |
| --- | --- |
| Compound 7 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

EXAMPLE D

| Emulsifiable Concentrate | |
| --- | --- |
| Compound 7 | 20.0% |
| blend of oil soluble sulfonates and polyoxyethylene ethers | 10.0% |
| isophorone | 70.0%. |

The compounds of this invention are useful as plant disease control agents. The present invention therefore further comprises a method for controlling plant diseases caused by fungal plant pathogens comprising applying to the plant or portion thereof to be protected, or to the plant seed or seedling to be protected, an effective amount of a compound of the invention or a fungicidal composition containing said compound. The compounds and compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, vegetable, field, cereal, and fruit crops. These pathogens include *Plasmopara viticola, Phytophthora infestans, Peronospora tabacina, Pseudoperonospora cubensis, Pythiunz aphanidermatum, Alternaria brassicae, Septoria nodorum, Septoria tritici, Cercosporidium personatum, Cercospora arachidicola, Pseudocercosporella herpotrichoides, Cercospora beticola, Botrytis cinerea, Monilinia fructicola, Pyricularia oryzae, Podosphaera leucotricha, Venturia inaequalis, Erysiphe graminis, Uncinula necatur, Puccinia recondita, Puccinia graminis, Hemileia vastatrix, Puccinia striiformis, Puccinia arachidis, Rhizoctonia solani, Sphaerotheca fuliginea, Fusarium oxysporum, Verticilliurm dahliae, Pythium aphanidermatum, Phytophthora megasperma, Sclerotinia sclerotiorum, Sclerotium rolfsii, Erysiphe polygoni, Pyrenophora teres, Gaeumannomycyes graminis, Rynchosporium secalis, Fusarium roseum, Bremia lactucae* and other generea and species closely related to these pathogens.

Compounds of this invention can also be mixed with one or more other insecticides, fungicides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection. Examples of such agricultural protectants with which compounds of this invention can be formulated are: insecticides such as abamectin, acephate, azinphos-methyl, bifenthrin, buprofezin, carbofuran, chlorfenapyr, chlorpyrifos, chlorpyrifos-methyl, cyfluthrin, beta-cyfluthrin, cyhalothrin, lambda-cyhalothrin, deltamethrin, diafenthiuron, diazinon, diflubenzuron, dimethoate, esfenvalerate, fenoxycarb, fenpropathrin, fenvalerate, fipronil, flucythrinate, tau-fluvalinate, fonophos, imidacloprid, isofenphos, malathion, metaldehyde, methamidophos, methidathion, methomyl, methoprene, methoxychlor, methyl 7-chloro-2,5-dihydro-2-[[N-(methoxycarbonyl)-N-[4-(trifluoromethoxy)phenyl]amino]carbonyl]indeno[1,2-e][1,3,4]oxadiazine-4a(3H)-carboxylate (DPX-JW062), monocrotophos, oxamyl, parathion, parathion-methyl, permethrin, phorate, phosalone, phosmet, phosphamidon, pirimicarb, profenofos, rotenone, sulprofos, tebufenozide, tefluthrin, terbufos, tetrachlorvinphos, thiodicarb, tralomethrin, trichlorfon and triflumuron; fungicides such as azoxystrobin, benomyl, blasticidin-S, Bordeaux mixture (tribasic copper sulfate), bromuconazole, captafol, captan, carbendazim, chloroneb, chlorothalonil, copper oxychloride, copper salts, cymoxanil, cyproconazole, cyprodinil (CGA 219417), diclomezine, dicloran, difenoconazole, dimethomorph, diniconazole, diniconazole-M, dodine, edifenphos, epoxiconazole (BAS 480F), famoxadone, fenarimol, fenbuconazole, fenpiclonil, fenpropidin, fenpropimorph, fluazinam, fluquinconazole, flusilazole, flutolanil, flutriafol, folpet, fosetyl-aluminum, furalaxyl, hexaconazole, ipconazole, iprobenfos, iprodione, isoprothiolane, kasugamycin, kresoxim-methyl, mancozeb, maneb, mepronil, metalaxyl, metconazole, S-methyl 7-benzothiazolecarbothioate (CGA 245704), myclobutanil, neo-asozin (ferric methanearsonate), oxadixyl, penconazole, pencycuron, probenazole, prochloraz, propiconazole, pyrifenox, pyroquilon, quinoxyfen, spiroxamine (KWG4168), sulfur, tebuconazole, tetraconazole, thiabendazole, thiophanate-methyl, thiram, triadimefon, triadimenol, tricyclazole, triticonazole, validamycin and vinclozolin; nematocides such as aldoxycarb and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis, Bacillus thuringiensis* delta endotoxin, baculovirus, and entomopathogenic bacteria, virus and fungi.

In certain instances, combinations with other fungicides having a similar spectrum of control but a different mode of action will be particularly advantageous for resistance management. Preferred for better control of plant diseases caused by fungal plant pathogens (e.g., lower use rate or broader spectrum of plant pathogens controlled) or resistance management are mixtures of a compound of this invention with a fungicide selected from the group azoxystrobin, kasugamycin, flutolanil, probenazole, and pencycuron. Specifically preferred mixtures (compound numbers refer to compounds in Index Tables A–D) are selected from the group: compound 7 and azoxystrobin; compound 7 and kasugamycin; compound 7 and flutolanil; compound 7 and probenazole; compound 7 and pencycuron; compound 30 and azoxystrobin; compound 30 and kasugamycin; compound 30 and flutolanil; compound 30 and probenazole; and compound 30 and pencycuron.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (e. g., soil, sand or water) in which the plants to be protected are growing. The compounds can also be applied to the seed to protect the seed and seedling.

Rates of application for these compounds can be influenced by many factors of the environment and should be determined under actual use conditions. Foliage can normally be protected when treated at a rate of from less than 1 g/ha to 5,000 g/ha of active ingredient. Seed and seedlings can normally be protected when seed is treated at a rate of from 0.1 to 10 g per kilogram of seed.

The following TESTS demonstrate the control efficacy of compounds of this invention on specific pathogens. The pathogen control protection afforded by the compounds is not limited, however, to these species. See Index Tables A–D for compound descriptions. The following abbreviations are used in the Index Tables which follow: Ph=phenyl and CN=cyano. The abbreviation "Ex." stands for "Example"

and is followed by a number indicating in which example the compound is prepared.

INDEX TABLE A

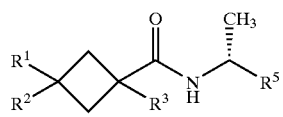

| Cmpd No. | $R^1$ | $R^2$ | $R^3$ | $R^5$ | mp (° C.) |
|---|---|---|---|---|---|
| 1 | $CH_3$ | Cl | $CF_3$ | 4-Br-Ph | 148–150 |
| 2 | $CH_3$ | Cl | $CF_3$ | $CH_2CH_2Ph$ | 106–109 |
| 3 | $CH_3$ | Cl | $CF_3$ | $CH_2O$-2-F-Ph | 66–69 |

INDEX TABLE B

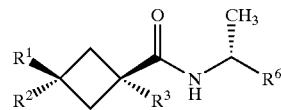

| Cmpd No. | $R^1$ | $R^2$ | $R^3$ | $R^6$ | mp (° C.) |
|---|---|---|---|---|---|
| 4 | $CH_3$ | Cl | $CF_3$ | 4-Br-Ph | 128–129 |
| 5 | Cl | $CH_3$ | $CF_3$ | 4-Br-Ph | 142–144 |
| 6 (Ex. 1) | $CH_3$ | Cl | $CF_3$ | 4-Cl-Ph | 129–130 |
| 7 (Ex. 1) | Cl | $CH_3$ | $CF_3$ | 4-Cl-Ph | 145–146 |
| 8 | $CH_3$ | Cl | $CF_3$ | 2,4-diCl-Ph | 149–150 |
| 9 | Cl | $CH_3$ | $CF_3$ | 2,4-diCl-Ph | 180–181 |
| 10 | $CH_3$ | Cl | H | 4-Br-Ph | 95–102 |
| 11 | Cl | $CH_3$ | H | 4-Br-Ph | 110–131 |
| 12 | Cl | Cl | Cl | 4-Br-Ph | 150 |
| 13 | $CH_3$ | Cl | $CH_3$ | 4-Br-Ph | 125–131 |
| 14 | Cl | $CH_3$ | $CH_3$ | 4-Br-Ph | 133–138 |
| 15 | Cl | $CH_3$ | Cl | 4-Br-Ph | 110–117 |
| 16 | $CH_3$ | Cl | Cl | 4-Br-Ph | 109–113 |
| 17 | Br | $CH_3$ | $CH_3$ | 4-Br-Ph | 139–142 |
| 18 | $CH_3$ | Br | $CH_3$ | 4-Br-Ph | 127–130 |
| 19 | $CH_3$ | Cl | $CH_3$ | 2,4-diCl-Ph | 178–193 |
| 20 | Cl | $CH_3$ | $CH_3$ | 2,4-diCl-Ph | 182–192 |
| 21 | $CH_3$ | Cl | $CH_3$ | 1-naphthylenyl | 143–147 |
| 22 | Cl | $CH_3$ | $CH_3$ | 1-naphthylenyl | 153–158 |
| 23 | $CH_3$ | Cl | $CH_3$ | 2-naphthylenyl | 72–86 |
| 24 | Cl | $CH_3$ | $CH_3$ | 2-naphthylenyl | 116–126 |
| 61 | $CH_2Cl$ | Cl | $CH_3$ | 4-Br-Ph | 93–113 |
| 62 | Cl | $CH_2Cl$ | $CH_3$ | 4-Br-Ph | 82–100 |
| 63 | $CH_2Cl$ | Cl | $CH_3$ | 2-naphthalenyl | 95–100 |
| 64 | Cl | $CH_2Cl$ | $CH_3$ | 2-naphthalenyl | 80–90 |
| 65 | $CH_3$ | Cl | $CH_2CH_3$ | 4-Br-Ph | 145–146 |
| 66 | Cl | $CH_3$ | $CH_2CH_3$ | 4-Br-Ph | 127–129 |
| 67 | F | F | $CH_3$ | 4-Br-Ph | 120–122 |
| 68 | $CH_3$ | Br | $CH_3$ | 2,4-diCl-Ph | 183–189 |
| 69 | Br | $CH_3$ | $CH_3$ | 2,4-diCl-Ph | 189–191 |

INDEX TABLE C

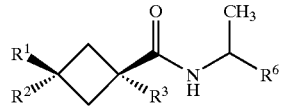

| Cmpd No. | $R^1$ | $R^2$ | $R^3$ | $R^6$ | mp (° C.) |
|---|---|---|---|---|---|
| 59 | Cl | $CH_3$ | $CH_3$ | 4-Br-2-$OCH_3$-Ph | 167–168 |
| 60 | $CH_3$ | Cl | $CH_3$ | 4-Br-2-$OCH_3$-Ph | 169–170 |
| 70 | $CH_3$ | F | $CH_3$ | 4-Br-2-$OCH_3$-Ph | 139–141 |
| 71 | $CH_3$ | Cl | $CH_3$ | 2,4-diCl-PH | 160–161 |
| 72 | Cl | $CH_3$ | $CH_3$ | 2,4-diCl-Ph | 178–180 |

INDEX TABLE D

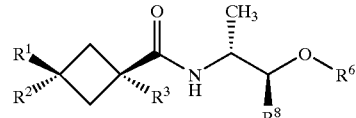

| Cmpd No. | $R^1$ | $R^2$ | $R^3$ | $R^6$ | $R^8$ | mp (° C.) |
|---|---|---|---|---|---|---|
| 25 | $CH_3$ | Cl | $CF_3$ | 2-F-Ph | H | 70–72 |
| 26 | Cl | $CH_3$ | $CF_3$ | 2-F-Ph | H | 87–89 |
| 27 | $CH_3$ | Cl | $CF_3$ | 2,5-diF-Ph | H | 77–79 |
| 28 | Cl | $CH_3$ | $CF_3$ | 2,5-diF-Ph | H | 99–101 |
| 29 (Ex. 2) | $CH_3$ | Cl | $CH_3$ | 2,5-diF-Ph | H | oil* |
| 30 (Ex. 2) | Cl | $CH_3$ | $CH_3$ | 2,5-diF-Ph | H | oil* |
| 31 | $CH_3$ | Cl | H | 2,5-diF-Ph | Ph | 139–141 |
| 32 | Cl | $CH_3$ | H | 2,5-diF-Ph | Ph | 144–147 |
| 33 | $CH_3$ | Cl | H | 2-CN-5-F-Ph | Ph | 55–65 |
| 34 | Cl | $CH_3$ | H | 2-CN-5-F-Ph | Ph | 60–70 |
| 35 | $CH_3$ | Cl | H | 2-CN-Ph | Ph | 54–66 |
| 36 | Cl | $CH_3$ | H | 2-CN-Ph | Ph | 57–70 |
| 37 | Cl | $CH_3$ | $CH_3$ | 4-Br-2-CN-Ph | H | 101–102 |
| 38 | $CH_3$ | Cl | $CH_3$ | 4-Br-2-CN-Ph | H | 122–123 |
| 39 | Cl | $CH_3$ | $CH_3$ | 4-F-2-CN-Ph | H | 86–88 |
| 40 | $CH_3$ | Cl | $CH_3$ | 4-F-2-CN-Ph | H | 113–114 |
| 41 | Cl | $CH_3$ | $CH_3$ | 4-Cl-2-CN-Ph | H | 100–101 |
| 42 | $CH_3$ | Cl | $CH_3$ | 4-Cl-2-CN-Ph | H | 128–129 |
| 43 | Cl | $CH_3$ | $CH_3$ | 5-F-2-CN-Ph | H | oil* |
| 44 | $CH_3$ | Cl | $CH_3$ | 5-F-2-CN-Ph | H | oil* |
| 45 | Cl | $CH_3$ | $CH_3$ | 5-Cl-2-CN-Ph | H | 107–108 |
| 46 | $CH_3$ | Cl | $CH_3$ | 5-Cl-2-CN-Ph | H | 77–79.5 |
| 47 | Cl | $CH_3$ | $CH_3$ | 5-Br-2-CN-Ph | H | 101.5–103 |
| 48 | $CH_3$ | Cl | $CH_3$ | 5-Br-2-CN-Ph | H | 100–103 |
| 49 | $CH_3$ | Cl | $CH_3$ | 2-Cl-5-F-Ph | H | 72–76 |
| 50 | Cl | $CH_3$ | $CH_3$ | 2-Cl-5-F-Ph | H | 77–84 |
| 51 | $CH_3$ | Cl | $CH_3$ | 5-Cl-2-F-Ph | H | 80–88 |
| 52 | Cl | $CH_3$ | $CH_3$ | 5-Cl-2-F-Ph | H | 78–83 |
| 53 | $CH_3$ | Br | $CH_3$ | 5-Cl-2-F-Ph | H | 86–87 |
| 54 | Br | $CH_3$ | $CH_3$ | 5-Cl-2-F-Ph | H | 83–84 |
| 55 | $CH_3$ | Br | $CH_3$ | 2-Cl-5-F-Ph | H | 68–69 |
| 56 | Br | $CH_3$ | $CH_3$ | 2-Cl-5-F-Ph | H | 74–76 |
| 57 | $CH_3$ | Br | $CH_3$ | 2,5-diF-Ph | H | 60–64 |
| 58 | Br | $CH_3$ | $CH_3$ | 2,5-diF-Ph | H | 68–71 |

*See Index Table E for $^1$H NMR data.

INDEX TABLE E $^1$H NMR Data (Me$_2$SO-d$_6$ solution unless indicated otherwise)$^a$

| Cmpd No. | |
|---|---|
| 29 | δ 1.14(d, 3H), 1.42(s, 3H), 1.52(s, 3H), 2.38(m, 2H), 2.82 (m, 2H), 3.99(d, 2H), 4.15(m, 1H), 6.70(m, 1H), 7.19 (m, 2H), 7.67(d, 1H). |
| 30 | δ 1.30(s, 3H), 1.58(d, 3H), 1.72(s, 3H), 2.27(m, 2H), 2.93 (m,2H), 3.99(m,2H), 4.15(m, 1H), 6.70(m, 1H), 7.18 (m, 2H), 7.61(d, 1H) |
| 43 | δ 1.32(d, J=6.6Hz, 3H), 1.57(s, 3H), 1.66(s, 3H), 2.47 (m, 1H), 2.51(m, 1H), 2.83(m, 1H), 2.88(m, 1H), 4.01(dd, J=4.2 and 1.2Hz, 2H), 4.36(m, 1H), 5.66(d,J= 7.5Hz, 1H), 6.72–6.82(m, 2H), 7.52(dd, J=8.7Hz and 7.2Hz, 1H) |
| 44 | δ 1.35(d, J=6.9Hz, 3H), 1.39(s, 3H), 1.76(s, 3H), 2.33 (m, 1H), 2.37(m, 1H), 2.98(m, 1H), 3.02(m, 1H), 4.04 (d, J=5.1Hz, 1H), 4.04(d, J=3.9Hz, 1H), 4.41(m, 1H), 5.82(d, J=7.5Hz, 1H), 6.76(dd, J=10.8 and 2.4Hz, 1H0, 6.81(dd, J=8.6 and 2.4Hz, 1H), 7.52(dd, J=8.6 and 7.7Hz, 1H) |

$^{a1}$H NMR data are in ppm downfield from tetramethylsilane. Couplings are designated by (s)-singlet, (d)-doublet, (m)-multiplet and (dd)-doublet of doublets. Coupling constants are indicated by J and reported in Hertz.

BIOLOGICAL EXAMPLES OF THE INVENTION

Test compounds were first dissolved in acetone in an amount equal to 3% of the final volume and then suspended at a concentration of 200 ppm in purified water containing 250 ppm of the surfactant Trem® 014 (polyhydric alcohol esters). The resulting test suspensions were then used in the following test. Spraying these 200 ppm test suspensions to the point of run-off on the test plants is the equivalent of a rate of 500 g/ha.

TEST A

The test suspension was sprayed to the point of run-off on wheat seedlings. The following day the seedlings were inoculated with a spore dust of *Erysiphe graminis* f. sp. *tritici*, (the causal agent of wheat powdery mildew) and incubated in a growth chamber at 20° C. for 7 days, after which disease ratings were made.

TEST B

The test suspension was sprayed to the point of run-off on wheat seedlings. The following day the seedlings were inoculated with a spore suspension of *Puccinia recondita* (the causal agent of wheat leaf rust) and incubated in a saturated atmosphere at 20° C. for 24 h, and then moved to a growth chamber at 20° C. for 6 days, after which disease ratings were made.

TEST C

The test suspension was sprayed to the point of run-off on rice seedlings. The following day the seedlings were inoculated with a spore suspension of *Pyricularia oryzae* (the causal agent of rice blast) and incubated in a saturated atmosphere at 27° C. for 24 h, and then moved to a growth chamber at 30° C. for 5 days, after which disease ratings were made.

TEST D

The test suspension was sprayed to the point of run-off on tomato seedlings. The following day the seedlings were inoculated with a spore suspension of *Phytophthora infestans* (the causal agent of potato and tomato late blight) and incubated in a saturated atmosphere at 20° C. for 24 h, and then moved to a growth chamber at 20° C. for 5 days, after which disease ratings were made.

TEST E

The test suspension was sprayed to the point of run-off on cucumber seedlings. The following day the seedlings were inoculated with a spore suspension of *Botrytis cinerea* (the causal agent of gray mold on many crops) and incubated in a saturated atmosphere at 20° C. for 48 h, and moved to a growth chamber at 20° C. for 5 days, after which disease ratings were made.

Results for Tests A–E are given in Table A. In the table, a rating of 100 indicates 100% disease control and a rating of 0 indicates no disease control (relative to the controls). A dash (-) indicates no test results. ND indicates disease control not determined due to phytotoxicity. # indicates significant activity.

TABLE A

| Cmpd No. | Test A | Test B | Test C | Test D | Test E |
|---|---|---|---|---|---|
| 1 | — | — | 100# | — | — |
| 2 | — | — | 64# | — | — |
| 3 | — | — | 82# | — | — |
| 4 | — | — | 100# | — | — |
| 5 | — | — | 100# | — | — |
| 6 | — | — | 98# | — | — |
| 7 | — | — | 100# | — | — |
| 8 | 0 | 0 | 100# | 24 | 0 |
| 9 | 0 | 0 | 100# | 0 | 0 |
| 10 | 74 | 0 | 53 | 42 | 0 |
| 11 | 57 | 0 | 53 | 60 | 0 |
| 12 | 99 | 0 | 100# | 11 | 0 |
| 13 | 0 | 0 | 94# | 0 | 0 |
| 14 | 0 | 0 | 97# | 0 | 0 |
| 15 | — | — | 94#* | — | — |
| 16 | — | — | 98#* | — | — |
| 17 | 0 | 0 | 74 | 0 | 0 |
| 18 | 0 | 0 | 99# | 0 | 0 |
| 19 | 33 | 0 | 100# | 0 | 0 |
| 20 | 59 | 0 | 100# | 0 | 0 |
| 21 | 0 | 0 | 0 | 0 | 0 |
| 22 | 0 | 0 | 0 | 0 | 0 |
| 23 | 0 | 0 | 97# | 0 | 0 |
| 24 | 0 | 0 | 100# | 0 | 0 |
| 25 | — | — | 97# | — | — |
| 26 | — | — | 100# | — | — |
| 27 | 72 | 0 | 99# | 14 | 0 |
| 28 | 53 | 0 | 100# | 0 | 0 |
| 29 | 0 | 86# | 100# | 0 | 0 |
| 30 | 0 | 0 | 100# | 0 | 94# |
| 31 | 0 | 0 | 90# | 0 | 0 |
| 32 | 59 | 0 | 52 | 0 | 0 |
| 33 | 0 | 0 | 52 | 0 | 0 |
| 34 | 59 | 0 | 52 | 45 | 0 |
| 35 | 0 | 0 | 86# | 0 | 0 |
| 36 | 0 | 0 | 0 | 0 | 0 |
| 37 | 0 | 25 | 0 | 23 | 8 |
| 38 | 0 | 66# | 0 | 23 | 8 |
| 39 | 0 | 25 | 97# | 45 | 47 |
| 40 | 0 | 0 | 0 | 62 | 0 |
| 41 | 0 | 0 | 0 | 85# | 19 |
| 42 | 63 | 0 | 0 | 43 | 19 |
| 43 | 0 | 0 | 0 | 20 | 19 |
| 44 | 0 | 0 | 94# | 20 | 84 |
| 45 | 0 | 0 | 99# | 61 | 0 |
| 46 | 63 | 28 | 91# | 43 | 0 |
| 47 | 97# | 25 | 94# | 26 | 0 |
| 48 | 96# | 85# | 99# | 47 | 0 |
| 49 | 98# | 0 | 100# | 0 | 0 |
| 50 | 54 | 0 | 94# | 0 | 0 |
| 51 | 83# | 0 | 100# | 0 | 0 |

TABLE A-continued

| Cmpd No. | Test A | Test B | Test C | Test D | Test E |
|---|---|---|---|---|---|
| 52 | 83# | 0 | 100# | 0 | 0 |
| 53 | 100# | 0 | 100# | 0 | 0 |
| 54 | 24 | 0 | 97# | 0 | 0 |
| 55 | 83# | 0 | 74 | 0 | 0 |
| 56 | 99# | 0 | 100# | 0 | 0 |
| 57 | 90# | 0 | 86# | 0 | 0 |
| 58 | 72 | 0 | 97# | 0 | 0 |
| 59 | 0 | 85# | 100# | 23 | 0 |
| 60 | 0 | 0 | 100# | 23 | 0 |
| 61 | 0 | 0 | 100# | 96# | 0 |
| 62 | 0 | 0 | 97# | 84# | 0 |
| 63 | 0 | 0 | 53 | 37 | 0 |
| 64 | 0 | 0 | 53 | 91# | 0 |
| 67 | 63 | 0 | 99# | 43 | 19 |
| 68 | 0 | 0 | 97# | 24 | 0 |
| 69 | 0 | 0 | 100# | 24 | 0 |
| 70 | 0 | 0 | 97# | 20 | 19 |
| 71 | 61 | 0 | 100# | 100# | 0 |
| 72 | 91# | 0 | 99# | 66 | 0 |

\* Tested at 40 ppm.

What is claimed is:

1. A compound selected from the formula

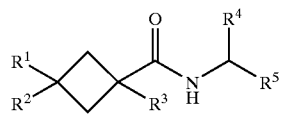

wherein
R$^1$ is halogen; C$_1$–C$_2$ alkoxy; C$_1$–C$_2$ haloalkoxy; or C$_1$–C$_2$ alkyl optionally substituted with halogen C$_1$–C$_2$ alkoxy or cyano;
R$^2$ is halogen; or C$_1$–C$_4$ alkyl optionally substituted with halogen, C$_1$–C$_2$ alkoxy or cyano;
R$^3$ is halogen; C$_1$–C$_4$ alkoxy; C$_1$–C$_4$ haloalkoxy; or C$_1$–C$_4$ alkyl optionally substituted with halogen, C$_1$–C$_2$ alkoxy or cyano or R$^2$ and R$^3$ can be taken together as —CH$_2$CH$_2$—;
R$^4$ is C$_1$–C$_2$ alkyl;
R$^5$ is R$^6$, CH(R$^8$)OR$^6$, CH(R$^8$)CH(R$^7$)R$^6$ or C(R$^8$)=C(R$^7$)R$^6$;
R$^6$ is naphthalenyl; a 5- to 6-membered aromatic heterocyclic ring containing 1 to 2 heteroatoms selected from nitrogen, oxygen and sulfur; or a 9- to 10-membered fused aromatic bicyclic ring containing 1 to 2 heteroatoms, each R$^6$ optionally substituted with one to three substituents selected from the group halogen, C$_1$–C$_4$ alkyl; C$_1$–C$_4$ haloalkyl, C$_1$–C$_4$ alkoxy, C$_1$–C$_4$ haloalkoxy, Si(CH$^3$)$^3$, cyano, NHC(=O)R$^9$ and NHC(=S)R$^9$;
R$^7$ is halogen, C$_1$–C$_4$ alkyl or C$_1$–C$_4$ haloalkyl;
R$^8$ is hydrogen, C$_1$–C$_6$ alkyl; phenyl optionally substituted with halogen, cyano, C$_1$–C$_3$ alkyl or C$_1$–C$_3$ alkoxy; or pyridinyl optionally substituted with halogen, cyano, C$_1$–C$_3$ alkyl or C$_1$–C$_3$ alkoxy; and
each R$^9$ is a hydrogen or C$_1$–C$_4$ alkyl;
provided that when R$^2$ and R$^3$ are taken together as —CH$_2$CH$_2$—, then R$^5$ is other than R$^6$.

2. A compound of claim 1 wherein
R$^1$ is halogen or C$_1$–C$_2$ alkyl optionally substituted with halogen;
R$^2$ is halogen or C$_1$–C$_2$ alkyl optionally substituted with halogen;
R$^3$ is halogen or C$_1$–C$_2$ alkyl optionally substituted with halogen;
R$^4$ is CH$_3$;
R$^5$ is R$^6$ or CH(R$^8$)OR$^6$.

3. A compound of claim 1 wherein
R$^1$ is halogen or C$_1$–C$_2$ alkyl;
R$^2$ is halogen or C$_1$–C$_2$ alkyl;
R$^3$ is C$_1$–C$_2$ allyl optionally substituted with halogen;
R$^4$ is CH$_3$;
R$^5$ is CH$_2$OR$^6$.

4. A fungicidal composition comprising a fungicidally effective amount of a compound and at least one other component selected from the group consisting of surfactants, solid diluents and liquid diluents wherein said compound is of the formula

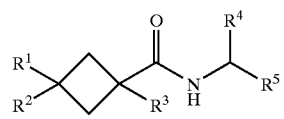

wherein
R$^1$ is halogen; C$_1$–C$_2$ alkoxy; C$_1$–C$_2$ haloalkoxy; or C$_1$–C$_2$ alkyl optionally substituted with halogen C$_1$–C$_2$ alkoxy or cyano;
R$^2$ is halogen; or C$_1$–C$_4$ alkyl optionally substituted with C$_1$–C$_2$ alkoxy or cyano;
R$^3$ is halogen; C$_1$–C$_4$ alkoxy; C$_1$–C$_4$ haloalkoxy; or C$_1$–C$_4$ alkyl optionally substituted with halogen, C$_1$–C$_2$ alkoxy or cyano or R$^2$ and R$^3$ can be taken together as —CH$_2$CH$_2$—;
R$^4$ is C$_1$–C$_2$ alkyl;
R$^5$ is R$^6$, CH(R$^8$)OR$^6$, CH(R$^8$)CH(R$^7$)R$^6$ or C(R$^8$)=C(R$^7$)R$^6$;
R$^6$ is naphthalenyl; a 5- to 6-membered aromatic heterocyclic ring containing 1 to 2 heteroatoms selected from nitrogen, oxygen and sulfur; or a 9- to 10-membered fused aromatic bicyclic ring containing 1 to 2 heteroatoms, each R$^6$ optionally substituted with one to three substituents selected from the group halogen, C$_1$–C$_4$ alkyl; C$_1$–C$_4$ haloalkyl, C$_1$–C$_4$ alkoxy, C$_1$–C$_4$ haloalkoxy, Si(CH$^3$)$^3$, cyano, NHC(=O)R$^9$ and NHC(=S)R$^9$;
R$^7$ is halogen, C$_1$–C$_4$ alkyl or C$_1$–C$_4$ haloalkyl;
R$^8$ is hydrogen, C$_1$–C$_6$ alkyl; phenyl optionally substituted with halogen, cyano, C$_1$–C$_3$ alkyl or C$_1$–C$_3$ alkoxy; or pyridinyl optionally substituted with halogen, cyano, C$_1$–C$_3$ alkyl or C$_1$–C$_3$ alkoxy; and
each R$^9$ is a hydrogen or C$_1$–C$_4$ alkyl;
provided that when R$^2$ and R$^3$ are taken together as —CH$_2$CH$_2$—, then R$^5$ is other than R$^6$.

5. A method for controlling plant diseases caused by fungal plant pathogens comprising applying to the plant or a portion thereof, or to the plant seed or seedling, a fungicidally effective amount of a compound of the formula

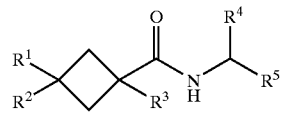

wherein
R$^1$ is halogen; C$_1$–C$_2$ alkoxy; C$_1$–C$_2$ haloalkoxy; or C$_1$–C$_2$ alkyl optionally substituted with halogen C$_1$–C$_2$ alkoxy or cyano;

$R^2$ is halogen; or $C_1$–$C_4$ alkyl optionally substituted with $C_1$–$C_2$ alkoxy or cyano;

$R^3$ is halogen; $C_1$–$C_4$ alkoxy; $C_1$–$C_4$ haloalkoxy; or $C_1$–$C_4$ allyl optionally substituted with halogen, $C_1$–$C_2$ alkoxy or cyano or $R^2$ and $R^3$ can be taken together as —$CH_2CH_2$—;

$R^4$ is $C_1$–$C_2$ alkyl;

$R^5$ is $R^6$, $CH(R^8)OR^6$, $CH(R^8)CH(R^7)R^6$ or $C(R^8)$=$C(R^7)R^6$;

$R^6$ is naphthalenyl; a 5- to 6-membered aromatic heterocyclic ring containing 1 to 2 heteroatoms selected from nitrogen, oxygen and sulfur; or a 9- to 10-membered fused aromatic bicyclic ring containing 1 to 2 heteroatoms, each $R^6$ optionally substituted with one to three substituents selected from the group halogen, $C_1$–$C_4$ alkyl; $C_1$–$C_4$ haloalkyl, $C_1$–$C_4$ alkoxy, $C_1$–$C_4$ haloalkoxy, $Si(CH^3)^3$, cyano, $NHC$(=O)$R^9$ and $NHC$(=S)$R^9$;

$R^7$ is halogen, $C_1$–$C_4$ alkyl or $C_1$–$C_4$ haloalkyl;

$R^8$ is hydrogen, $C_1$–$C_6$ alkyl; phenyl optionally substituted with halogen, cyano, $C_1$–$C_3$ alkyl or $C_1$–$C_3$ alkoxy; or pyridinyl optionally substituted with halogen, cyano, $C_1$–$C_3$ alkyl or $C_1$–$C_3$ alkoxy; and each $R^9$ is a hydrogen or $C_1$–$C_4$ alkyl;

provided that when $R^2$ and $R^3$ are taken together as —$CH_2CH_2$—, then $R^5$ is other than $R^6$.

6. A fungicidal composition comprising a fungicidally effective amount of a compound and at least one other component selected from the group consisting of surfactants, solid diluents and liquid diluents wherein said compound is of the formula

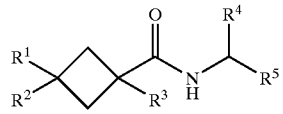

wherein $R^1$ is halogen or $C_1$–$C_2$ alkyl;

$R^2$ is halogen or $C_1$–$C_2$ alkyl;

$R^3$ is $C_1$–$C_2$ alkyl optionally substituted with halogen;

$R^4$ is $CH_3$;

$R^5$ is $R^6$; and $R^6$ is naphthalenyl optionally substituted with one to three substitutents selected form the group halogen, $C_1$–$C_4$ alkyl; $C_1$–$C_4$ haloalkoxy and cyano.

7. The composition of claim 6 wherein said compound is [1(R)-cis]-3-chloro-1,3-dimethyl-N-[1-(2-napthalenyl)ethyl]cyclobutanecarboxamide.

8. A method for controlling plant diseases caused by fungal plant pathogens comprising applying to the plant or a portion thereof, or to the plant seed or seedling, a fungicidally effective amount of a compound of the formula

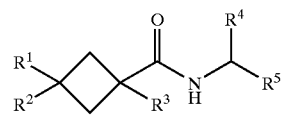

wherein $R^1$ is halogen or $C_1$–$C_2$ alkyl;

$R^2$ is halogen or $C_1$–$C_2$ alkyl;

$R^3$ is $C_1$–$C_2$ alkyl optionally substituted with halogen;

$R^4$ is $CH_3$;

$R^5$ is $R^6$; and $R^6$ is naphthalenyl optionally substituted with one to three substituents selected form the group halogen, $C_1$–$C_4$ alkyl; $C_1$–$C_4$ haloalkoxy and cyano.

9. The method of claim 8 wherein said compound is [1(R)-cis]-3-chloro-1,3-dimethyl-N-[1-(2-napthalenyl)ethyl]cyclobutanecarboxamide.

* * * * *